(12) United States Patent
Russak

(10) Patent No.: US 11,636,952 B2
(45) Date of Patent: Apr. 25, 2023

(54) SYSTEM AND METHOD OF MEASURING BODY FLUIDS

(71) Applicant: AZURE VAULT LTD., Ramat-Gan (IL)

(72) Inventor: Ze'ev Russak, Netanya (IL)

(73) Assignee: AZURE VAULT LTD., Ramat-Gan (IL)

( * ) Notice: Subject to any disclaimer, the term of this patent is extended or adjusted under 35 U.S.C. 154(b) by 517 days.

(21) Appl. No.: 16/623,758

(22) PCT Filed: Jun. 30, 2018

(86) PCT No.: PCT/IB2018/054878
§ 371 (c)(1),
(2) Date: Dec. 17, 2019

(87) PCT Pub. No.: WO2019/012368
PCT Pub. Date: Jan. 17, 2019

(65) Prior Publication Data
US 2020/0126674 A1    Apr. 23, 2020

(30) Foreign Application Priority Data
Jul. 11, 2017 (WO) .................. PCT/IB2017/054161

(51) Int. Cl.
*G16H 50/50* (2018.01)
*G16H 10/40* (2018.01)
(Continued)

(52) U.S. Cl.
CPC ............ *G16H 50/50* (2018.01); *A61B 5/0008* (2013.01); *A61B 5/01* (2013.01); *A61B 5/1172* (2013.01);
(Continued)

(58) Field of Classification Search
CPC ...... G16H 50/50; G16H 10/40; A61B 5/0008; A61B 5/01; A61B 5/1172; A61B 5/150022; A61B 5/157; A61B 5/150229; A61B 5/14532; A61B 2560/0247; A61B 5/145; A61B 5/15113; A61B 5/15142;
(Continued)

(56) References Cited

U.S. PATENT DOCUMENTS

2005/0069925 A1* 3/2005 Ford .................... A61B 5/4266
702/20
2008/0138793 A1    6/2008 Lindberg et al.
(Continued)

OTHER PUBLICATIONS

International Search Report issued in PCT/IB2018/054878 dated Jun. 20, 2019 (2 pages).
(Continued)

*Primary Examiner* — Eliza A Lam
(74) *Attorney, Agent, or Firm* — Acuity Law Group, PC; Michael A. Whittaker

(57) ABSTRACT

A method of measuring body fluid content, the method comprising computer executed steps, the steps comprising: receiving a value of a temperature of a body part of a subject, and generating corrective data based on the received measured temperature value and on previously gathered data, the corrective data being usable for correcting a measurement of content of a fluid sample taken from the body part.

20 Claims, 7 Drawing Sheets

(51) Int. Cl.
   *A61B 5/00* (2006.01)
   *A61B 5/01* (2006.01)
   *A61B 5/1172* (2016.01)
   *A61B 5/15* (2006.01)
   *G06T 7/00* (2017.01)
   *G06V 40/13* (2022.01)

(52) U.S. Cl.
   CPC ...... *A61B 5/150022* (2013.01); *G06T 7/0012* (2013.01); *G06V 40/13* (2022.01); *G16H 10/40* (2018.01)

(58) Field of Classification Search
   CPC ... A61B 5/7221; A61B 5/7203; G06T 7/0012; G06V 40/13; G06F 7/66
   See application file for complete search history.

(56) References Cited

U.S. PATENT DOCUMENTS

| | | |
|---|---|---|
| 2009/0030641 A1 | 1/2009 | Fjield et al. |
| 2014/0323836 A1 | 10/2014 | Kusukame et al. |
| 2015/0119669 A1 | 4/2015 | Feldman et al. |
| 2015/0317855 A1* | 11/2015 | Sezan ................ A61B 5/14532 340/5.52 |
| 2016/0069743 A1* | 3/2016 | McQuilkin .......... G01N 21/255 356/416 |

OTHER PUBLICATIONS

Written Opinion issued in PCT/IB2018/054878 dated Jun. 20, 2019 (6 pages).

\* cited by examiner

SYSTEM AND METHOD OF MEASURING BODY FLUIDS

CROSS-REFERENCE TO RELATED APPLICATIONS

The present invention is filed under 35 U.S.C. § 371 as the United States national phase of International Application No. PCT/IB2018/054878, filed Jun. 30, 2018, which designated the United States and which claims the benefit of priority to International Patent Application No. PCT/IB2017/054161, filed Jul. 11, 2017, each of which is herein incorporated by reference.

FIELD AND BACKGROUND OF THE INVENTION

The present invention relates to body fluid measurement and more particularly, but not exclusively to a device, system and method of measuring a subject's body fluid content based on the content of a sample taken from a body part of the subject.

There are many currently available devices for taking fluid (say blood) samples from a subject's (say person's) body part (say from a person's finger, by taking venous blood from one of the finger's veins).

Indeed, in recent years, the numbers of persons who suffer from various chronic diseases such as diabetes have been soaring. For those persons, self administered examination of blood sugar level, etc., using blood sampling devices, over the course of their regular day has become a part of their life.

In recent years, diseases transmitted through the blood have also become a social issue.

To prevent AIDS, Hepatitis, and other serious diseases, devices that enable a patients himself or rather a nurse or physician, to accurately sample the patient's blood and measure the blood's content without problem would be needed. However, for various reasons, devices in current use have not proved accurate enough for measuring contents of body fluid samples.

For example, blood samples are often taken from patients using a finger stick or a tube. A fluid sample taken this way is difficult to analyze accurately. For example, such a blood sample may be subject to clotting which may distort quantitative measurement, and even damage a device used to take the sample, say by clogging a small tube in a blood analyzer in use on the device, as known in the art.

Similarly, measured quantities of some pathogens in body fluids, such as blood parasites in blood samples, can be influenced by the physical properties of the capillaries from which the blood is taken, due to blood cells size, elasticity and stickiness.

SUMMARY OF THE INVENTION

According to one aspect of the present invention there is provided a method of measuring body fluid content, the method comprising computer executed steps, the steps comprising: receiving a measured value of a temperature of a body part of a subject, and generating corrective data based on the received measured temperature value and on previously gathered data, the corrective data being usable for correcting a measurement of content of a fluid sample taken from the body part.

According to a second aspect of the present invention there is provided an apparatus for measuring body fluid content, the apparatus comprising: a computer processor, a temperature receiver, implemented on the computer processor, configured to receive a measured value of a temperature of a body part of a subject, and a corrective data generator, configured to generate corrective data based on the received measured temperature value and on previously gathered data, the corrective data being usable for correcting a measurement of content of a fluid sample taken from the body part.

According to a third aspect of the present invention there is provided a non-transitory computer readable medium storing computer executable instructions for performing steps of measuring body fluid content, the steps comprising: receiving a measured value of a temperature of a body part of a subject, and generating corrective data based on the received measured temperature value and on previously gathered data, the corrective data being usable for correcting a measurement of content of a fluid sample taken from the body part.

According to a fourth aspect of the present invention there is provided a method for measuring body fluid content, the method comprising steps carried out by a computer processor, the steps comprising: receiving a value of a measured temperature of a body part of a subject, sending the measured temperature value to a computer, receiving corrective data generated based on the sent measured temperature value and on data previously gathered on the computer, from the computer, and correcting a measurement of content of a fluid sample taken from the body part, using the received corrective data.

According to a fifth aspect of the present invention there is provided an apparatus for measuring body fluid content, the apparatus comprising: a computer processor, a temperature receiver, implemented on the computer processor, configured to receive a measured value of a temperature of a body part of a subject, and a temperature sender, in communication with the temperature receiver, configured to send the measured temperature value to a computer, a corrective data receiver, implemented on the computer processor, configured to receive corrective data generated based on the sent measured temperature value and on data previously gathered on the computer, from the computer, and a measurement corrector, in communication with the corrective data receiver, configured to correct a measurement of content of a fluid sample taken from the body part, using the received corrective data.

According to a sixth aspect of the present invention there is provided a non-transitory computer readable medium storing computer processor executable instructions for performing steps of measuring body fluid content, the steps comprising: receiving a measured value of a temperature of a body part of a subject, sending the measured temperature value to a computer, receiving corrective data generated based on the sent temperature value and on data previously gathered on the computer, from the computer, and correcting a measurement of content of a fluid sample taken from the body part, using the received corrective data.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings.

DESCRIPTION OF THE PREFERRED EMBODIMENTS

Figure 1:
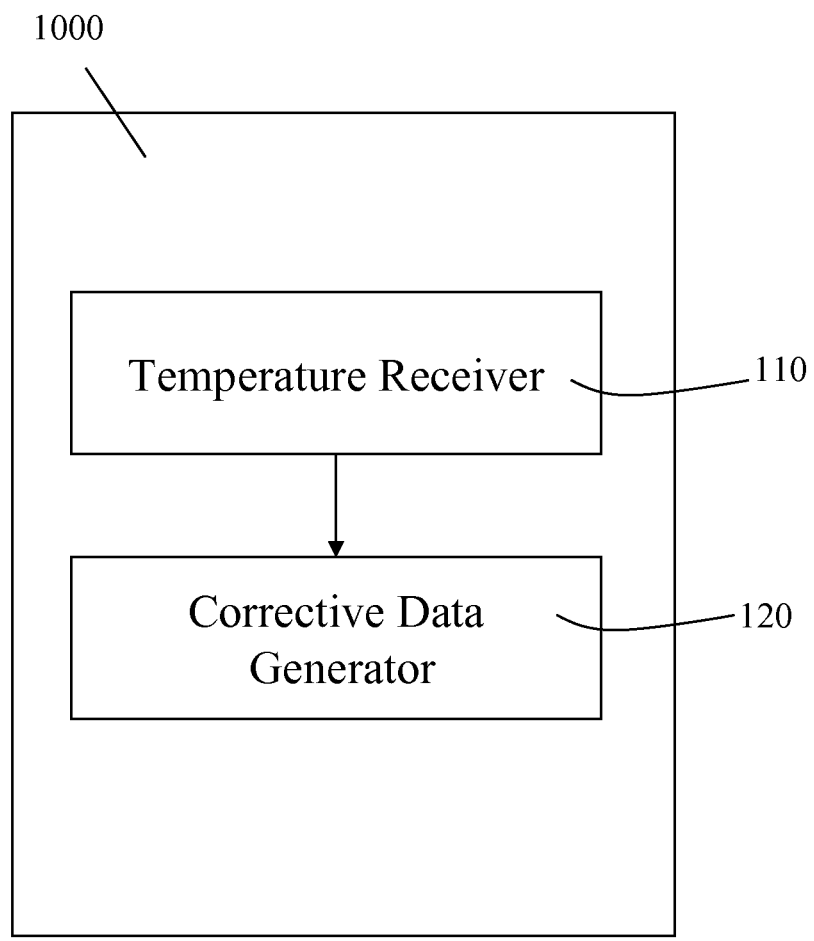
FIG. 1 is a simplified block diagram schematically illustrating a first exemplary apparatus for measuring body fluid content, according to an exemplary embodiment of the present invention.

The present embodiments comprise an apparatus and a method of measuring body fluid in general, and body fluid content in particular.

Today, fluid samples (say blood samples) are often taken from subjects using a finger stick, a tube, etc.

However, a fluid sample taken this way may be difficult to analyze accurately.

For example, a blood sample taken from a subject's body part (say from a finger or arm) may be subject to clotting which may distort quantitative measurement, and even damage a device used to take the blood sample, say by clogging one of the small tubes of a blood analyzer in use on the device, as known in the art.

Similarly, measured quantities of some pathogens in body fluids, such as blood parasites in a blood sample, can be influenced by the physical properties of the capillaries from which the blood is taken, say due to blood cells size, elasticity and stickiness.

An invention of at least some of the present embodiments recognizes that measurements of contents of a fluid sample taken from a subject may need to be corrected based on the temperature of a body part (say an arm, a finger, an internal body organ, etc.) from which the fluid sample is taken. The temperature of the body part may be measured while taking the sample, a few seconds or milliseconds before taking the sample, or a few seconds or milliseconds after taking the sample, as described in further detail hereinbelow.

For example, bleeding time and clotting time may depend on temperature of a body part from which a blood sample is taken, and may potentially influence the measurement of the concentrations of blood elements, sugar, pathogens, etc., in the blood sample, such that the measured concentrations may be less accurate.

Thus, according to an exemplary embodiment of the present invention, in one example, there is received a value of a temperature of a body part (say a finger, arm, stomach, or other body organ) of a subject as measured by a device used to take a fluid sample (say a blood sample) from the body part.

The temperature value may be measured by the device while taking the fluid sample, a few seconds or milliseconds before taking the sample, a few seconds or milliseconds after taking the sample, etc., or any combination thereof (say by averaging over temperature values measured while taking the sample).

Next, based on the received temperature value and on previously gathered data, there is generated corrective data that is usable for correcting a measurement of content of the fluid sample by the device.

In one example, the previously gathered data comprises for each one of two or more of previously taken test samples, a respective temperature value measured when taking the test sample, a respective content value measured using the test sample, other parameter values, etc., as described in further detail hereinbelow.

In the example, the corrective data defines a function calculated over the previously gathered data, say using linear regression or another multi-parametric fitting method (say using Neural Networks, a Non-linear Manifold learning method such as Diffusion Mapping, etc.), as described in further detail hereinbelow.

Then, in the exemplary embodiment, a measurement of a content of the fluid sample as made immediately after taking the sample is corrected using the corrective data, say by replacing a result of that measurement with a value or rather with a range of values, as described in further detail hereinbelow.

Optionally, the temperature value is received with biometric data taken by the device from the body part of the subject, and the biometric data is used for determining which samples belong to a same subject, as described in further detail hereinbelow. In one example, the body part is a finger of the subject, and the biometric data includes fingerprint data taken by the device from the finger using a finger scanner, as known in the art.

Optionally, in the exemplary embodiment, there is further generated disease progress data (say data on the disease stage that the subject is in) based on the previously gathered data, the received temperature value, etc., as described in further detail hereinbelow.

Optionally, in the exemplary embodiment, there is further cooled or warmed the body part into a predetermined temperature value prior to taking the fluid sample from the body part using the device, say using a thermoelectric cooler (TEC), a heating element, etc., as described in further detail hereinbelow.

Optionally, in the exemplary embodiment, there is further captured an image of the body part (say the user's finger, upper arm part, etc.). The image may be captured, for example, using a visible light camera, an IR (Infra Red) Camera, etc., say using a camera installed on the device, as described in further detail hereinbelow. The camera may be automatically or manually triggered, so as to capture the image, as described in further detail hereinbelow.

The captured image may be used for guiding a user when taking the fluid sample, as described in further detail hereinbelow.

In one example, the fluid sample is to be taken from the user's finger.

In the example, the device has an at least partially transparent area (say a plastic surface), on which area the user has to position his finger before the device pricks the finger, and a camera installed on the device, under that area, as described in further detail hereinbelow. In the example, when the user positions his finger on the at least partially transparent area, the device automatically captures a picture of the finger with the camera.

Then, the captured image of the user's finger may be analyzed, say for identifying previous pricks on the finger, for counting the number of the pricks present on the finger, for identifying traces of blood on the finger, etc., or any combination thereof.

As a part of the analysis, there may be determined which area of the finger is better suited for taking the fluid (say blood) sample, whether the user should rather take the sample from another one of the user's fingers, etc., as described in further detail hereinbelow.

Based on the analysis of the captured image, the user may be guided in taking the fluid sample, say using messages presented on a small (say a Liquid Crystal Display (LCD)) screen that may be installed on the device, using vocal instructions given to the user using one or more speakers that may be installed on the device, etc., as described in further detail hereinbelow.

Thus, in one example, the user may be advised to take the fluid sample from another one of his fingers since the finger is over-pricked (say when the number of pricks identified on the finger in the analysis of the captured image exceeds a threshold predefined by a programmer of a computer processor installed on the device), has some areas that are covered with traces of blood that may be indicative of fresh bleeding from previous pricking, etc.

In a second example, the user may be asked to change the orientation of his finger when positioned on the device, so as to allow the device to prick the finger at the area of the finger determined to be better suited for taking the fluid sample, etc., as described in further detail hereinbelow.

After the user changes the finger's orientation or positions another finger on the device, the camera may be automatically or manually triggered, so as to capture a new image (i.e. an image of the other finger or of the old finger in the new orientation), and the new image is similarly analyzed, as described in further detail hereinbelow.

Optionally, in the exemplary embodiment, on the device used to take the fluid sample, there is alternatively or additionally measured an electric property of the taken sample (say a one indicative of pH of the sample), an optical property of the taken sample (say a one indicative of hemoglobin content of the sample), etc., as described in further detail hereinbelow.

Optionally, in the exemplary embodiment, on the device used to take the fluid sample, there is alternatively or additionally carried out a chemical process on the taken fluid sample, as described in further detail hereinbelow.

Thus, potentially, with the present embodiments, measurements of contents of a fluid sample taken from a subject may be made more accurate, using corrective data that is generated based on the body part's temperature.

Indeed, a change in the body part's temperature may have a potential to impact on the measurements, say by changing blood cell elasticity and stickiness.

Accordingly, a correction of the measurements according to the body part's temperature does have a potential of improving the measurements' accuracy, as described in further detail hereinbelow.

Further, with present embodiments, a warming or cooling of the subject's body part from which the sample is taken, may further improve the accuracy, especially when pushing the body part's temperature into a temperature range that may prove advantageous (say in as far as blood clotting, stickiness, etc., are concerned).

Furthermore, with present embodiments, a picture of the body part (say a finger) as taken prior to taking the fluid sample may be analyzed, say for determining which area of the finger is better suited for taking the fluid (say blood) sample, whether the user should rather take the sample from another one of the user's fingers, etc. The analyzed picture may then be used for guiding the user, say by instructing the user to take the fluid sample from another one of the user's fingers since the finger is over-pricked, thus potentially improving the accuracy, as described in further detail hereinbelow.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1, which is a simplified block diagram schematically illustrating a first exemplary apparatus for measuring body fluid content, according to an exemplary embodiment of the present invention.

Apparatus 1000 for measuring body fluid content may be implemented using electric circuits, computer software, computer hardware, etc.

Optionally, at least some parts of the apparatus 1000 are implemented on a computer processor of a device used to take fluid samples from subjects (say persons, animals, etc.), say on the device described in further detail hereinbelow and illustrated using FIG. 3.

Optionally, at least some parts of the apparatus 1000 are implemented on a computer in communication with the device used to take the fluid samples. The communication may be remote (say a communication over the internet), short-ranged (say a communication over a LAN (local Area network) or a Wi-Fi Connection), etc., as described in further detail hereinbelow.

Thus, the apparatus 1000 includes a computer processor.

The apparatus 1000 further includes one or more additional parts described in further detail hereinbelow, such as the parts 110-120 shown in FIG. 1, and described in further detail hereinbelow.

The additional parts may be implemented as software—say by programming the computer processor to execute the steps of the method described in further detail and illustrated using FIG. 4 hereinbelow, as hardware—say as an electric circuit that implements at least a part of that method, etc., or any combination thereof.

More specifically, the apparatus 1000 includes a temperature receiver 110, implemented on the computer processor.

The temperature receiver 110 receives a value of a temperature of a subject's body part that a fluid sample is taken from, as measured while taking the sample, a few (say less than thirty) seconds or milliseconds before taking the sample, a few seconds or milliseconds after taking the sample, etc., as described in further detail hereinbelow.

The temperature may be measured by the device used to take the sample (say using a thermometer installed on the device), by a device (say an electronic thermometer) used together with the device used to take the sample, etc., as described in further detail hereinbelow, for example in FIG. 3.

Optionally, the temperature receiver additionally or alternatively receives other parameters with the value of the temperature of the subject's body part, say an ambient temperature value measured by the device used to take the sample or by the device used therewith when taking the sample, etc., and possibly, also a measured value of a content of the sample to be corrected, as described in further detail hereinbelow.

In one example, the apparatus 1000 is implemented on the device used to take the fluid sample. In the example, the temperature value is received from one of the parts of the device—say from a temperature measurer of the device, as described in further detail hereinbelow and illustrated using FIG. 3.

In another example, the apparatus 1000 is implemented on a computer in communication with the device used to take the fluid sample, in which case the temperature value is received by the computer from the device through the computer's communication with the device, as described in further detail hereinbelow.

The apparatus 1000 further includes a corrective data generator 120, in communication with the temperature receiver 110, which corrective data generator 120 is also implemented on the computer processor.

The corrective data generator 120 generates corrective data (say data defining a function having one or more parameters) based on the temperature value received by the temperature receiver 110 and on previously gathered data, as described in further detail hereinbelow.

Optionally, the corrective data's generation by the corrective data generator 120 is further based on one or more additional parameters received with the body part's temperature value, as described in further detail hereinbelow.

The corrective data is usable for correcting a measurement of a content of the fluid sample by the device used to take the sample, say a measurement of a specific pathogen's concentration in a person's blood as measured by the device using a blood sample taken from the person, as described in further detail hereinbelow.

In a first example, the apparatus 1000 is implemented on the device and further includes a measurement corrector in communication with the corrective data generator 120, as described in further detail hereinbelow. In the example, the measurement corrector corrects the measurement of the sample as carried out by the device, using the corrective data, as described in further detail hereinbelow.

In the first example, the apparatus 1000 further includes a sample taker—say a one made of a blood drawing component (say a one with a lancet or needle used to prick the body part), one or more tubes, one or more storage compartments (say a vial or one or more lab-on-a-chip's compartments) and a pump that is operable by a user or that is triggered automatically, for pumping the sample from the body part to the compartment(s).

In the first example, the apparatus 1000 further includes a content measurer, implemented on the device, in communication with the sample taker and the measurement corrector.

The content measurer measures the content of the sample, say by taking measurements of the concentration of a specific pathogen in the fluid sample, and hence in the subject's body fluid (say the concentration of a specific parasite in the subject's blood), as described in further detail hereinbelow.

Optionally, the content measurer measures the pathogen's concentration using a chemical process such as a DNA polymerization based chain process (say PCR) carried out in the compartment(s), say using one or more fluorescence readers, voltmeters, etc., that may be installed next to the compartment(s) or connected thereto, as known in the art.

In one example, the process uses different types of molecules, where each type's Y-shaped molecules have a single-stranded DNA or antibody attached to the Y-shaped molecule's base and designed to pair with complementary DNA of a specific, different pathogen. That is to say that for each type, the pathogen is different from a pathogen that molecules of another one of the types would pair with, as known in the art.

Each Y-shaped molecule further has a molecule attached to one of the upper arms of the Y-shaped molecule. In the presence of ultraviolet (UV) light, when the Y-shaped molecule is paired with the complementary DNA using the single stranded DNA or antibody, the molecule attached to the upper arm chains up with similar molecules.

In the example, the Y-shaped molecules are added in advance to the compartments—say by filling each specific one of the compartments with Y-shaped molecules of a different, specific one of the types only.

When the specific pathogen matched by Y-shaped molecules of one of the types is present in the taken fluid sample, the Y-shaped molecules in the specific compartment lock onto the pathogen. Further, in the presence of ultraviolet light that is emitted using a light source installed on the device, next to the compartment, the Y-shaped molecules, when paired with the pathogen's DNA, link to form long chains of Y-molecules.

As a result, with the pathogen present and the UV light emitted from the light source, a resulting chain reaction is easily detected in the compartment, and the reaction omits fluorescence at a level that may be measured by the fluorescence reader. Then, the measured level is used to by the content measurer, to assess the pathogen's concentration in the fluid sample.

In the first example, the fluid sample is taken by the device, the sample's content is measured by the device, and the measurement of the content is corrected by the device based on the corrective data generated by the device, as described in further detail hereinbelow.

In a second example, at least some parts of the apparatus 1000 are implemented on the computer in communication with the device, as described in further detail hereinbelow.

In the second example, the apparatus 1000 further includes a corrective data sender that is implemented on the computer and that is in communication with the corrective data generator 120. In the example, the corrective data sender sends the generated corrective data to the device used to take the sample, say to the measurement corrector that in the second example too, is implemented on that device. The measurement corrector corrects the measurement of the sample as carried out on the device, using the corrective data received from the corrective data sender, as described in further detail hereinbelow.

Thus, in the second example, the fluid sample is taken by the device, the sample's content is measured by the device, and the measurement of the content is corrected by the device based on the corrective data generated on the computer in communication with the device and sent from the computer to the device.

In a third example, the apparatus 1000 is implemented on the computer that is in communication with the device, and the apparatus 1000 includes the measurement corrector that in the third example, is implemented on the computer's processor. That is to say that in the third example, the measurement corrector too is implemented on the computer that is in communication with the device used to take the fluid sample rather than on the device used to take the fluid sample.

More specifically, in the third example, the measurement corrector implemented on the computer's processor receives a result of the measurement of the content of the fluid sample (i.e. a measured value) from the device used to take the sample and corrects the measurement using the corrective data generated by the corrective data generator 120, as described in further detail hereinbelow.

In the third example, the computer may communicate the corrected result back to the device, for the device to display the corrected result to the user (say on small screen installed on the device), or rather allow a user of the computer to check the corrected result online (say using a web browser).

Thus, in the third example, the fluid sample is taken by the device and the sample's content is measured by the device. However, the measurement is corrected by the computer in communication with the device, based on the corrective data generated by the computer, by correcting the result that the computer receives from the device used to take the fluid sample.

The measurement corrector (whether implemented on the device used to take the fluid sample or on the computer in communication therewith) may correct the measurement by replacing the measurement's result value with a value, by replacing the value with a range of values, etc., as described in further detail hereinbelow.

In a first example, the corrective data generated by the corrective data generator 120 defines a function that when applied to the measurement's result (say by the measurement corrector), yields a range of values.

In the example, the measurement corrector corrects the measurement using the corrective data whenever a result of the measurement is out of that value range based on the corrective data, say by replacing the result with the closest value that is still within the range (say with the maximal or minimal value of the range).

In a second example too, the corrective data generated by the corrective data generator 120 defines a function that when applied to the measurement's result (say by the measurement corrector), yields a range of values. However, in the second example, the measurement corrector always replaces the result with the value range based on the corrective data (i.e. regardless on the result's being within that range or out of that range).

Optionally, the previously gathered data that the corrective data generator 120 uses for generating the corrective data includes data on two or more previously taken fluid test samples, each of which samples is also referred to hereinbelow as a 'test sample'.

More specifically, the data on the previously taken fluid samples includes for each one of the fluid samples, at least two parameters—namely, a respective temperature value measured when taking that sample and a respective content value measured using that sample.

Optionally, for each one of the previously taken samples, the data further includes one or more additional parameters.

The additional parameters may include, but are not limited to: a time indication (say a one that indicates a time of taking of the respective sample, whether absolute or relative to a start of a series made of at least some of the test samples), or an ambient temperature measured when taking the test sample, as described in further detail hereinbelow.

The parameters may also include, an alternative measurement value (say a one obtained using a device different from a device used to take the test sample), a light reading (say for assessing blood oxygen saturation), hemoglobin level, a temperature of a body part other than the one that the test sample is taken from, etc.

Optionally, the parameters received for the test samples, are historic values gathered by the device or historic value received by the computer from the device, and/or from similar devices, or any combination thereof, as described in further detail hereinbelow.

Optionally, the temperature receiver 110 further receives with the temperature value, biometric data taken from the subject.

Optionally, the biometric data is taken by the device from the body part that the fluid sample is taken from or rather, from another body part of the subject, during the fluid sample's taking, as described in further detail hereinbelow, and as illustrated, for example, in FIG. 3. For example, the biometric data may include fingerprint data taken from the subject's finger used to take the fluid sample from.

The biometric data may be used for determining which samples belong to a same subject.

Thus, in one example, the parameters received for each one of the test samples include an image of a fingerprint taken from a subject's finger when taking the test sample (say a blood sample) from that finger.

In the example, the corrective data generator 120 selects test samples to be used for generating the corrective data (say the data defining a function) from the previously gathered data, using the fingerprint data received for the sample subject to the measurement to be corrected, together with the temperature value.

Specifically, in the example, the corrective data generator 120 uses the fingerprint data received with the temperature value, by the temperature receiver 110, to select only historic values that belong to test samples taken from the same subject that the fingerprint data belongs to, for the corrective data to be based on.

After selecting the historic values using the fingerprint data, the corrective data generator 120 generates the corrective data based on the parameters received for the selected test samples—i.e. from samples taken from a same subject as that of the sample for which the measurement is to be corrected using the corrective data, as described further detail hereinbelow.

Optionally, the apparatus 1000 further includes a disease progress data generator in communication with the temperature receiver 110.

The disease progress data generator generates disease progress data (say an indication on a stage of a disease that the subject suffers from) based on the previously gathered data, say using a disease progress clinical estimate model calculated using a learning machine method, as described in further detail hereinbelow.

Optionally, the apparatus 1000 further includes a temperature controller, say a one implemented on the computer processor of the device used to take the fluid sample.

The temperature controller changes the temperature of the body part prior to the taking of the fluid sample from the body part by the device, say by controlling a thermoelectric cooler (TEC), a heating element, etc., or any combination thereof, as described in further detail hereinbelow.

In one example, the temperature controller changes the body part's temperature into a temperature value that is predefined by a programmer or operator of the device or of the computer in communication with the device, as described in further detail hereinbelow.

Preferably, the temperature value is predefined—say so as to be optimal for the measurement's type (say for a specific type of parasite quantitative measurement in blood samples), for environmental parameters such as ambient temperature or humidity, as learnt from scientific literature, previous measurements, etc., or so as to give uniform conditions for all samples taken for a same subject.

In one example, the device also includes a pump used to draw the fluid sample from the body part. In the example, the pump draws the fluid sample from the body part only after the temperature controller changes the body part's temperature into the predefined temperature value.

Thus in the example, the body part is cooled or warmed into the predetermined temperature value prior to taking the fluid sample from the body part using the device.

The warming or cooling of the subject's body part may further improve the accuracy of measurement of the content, especially when pushing the body part's temperature into a temperature range that may prove advantageous (say in as far as blood clotting, stickiness, etc., are concerned), as described in further detail hereinbelow.

Optionally, the device used to take the fluid sample further includes an image capturer, say a scanner or a camera used to capture an image of the body part (say the user's finger, upper arm part, etc.) prior to the taking of the fluid sample from that body part, as described in further detail hereinbelow. The camera may be a visible light camera, an IR (Infra Red) Camera, etc., as known in the art.

The captured image may be used for guiding a user when taking the fluid sample, as described in further detail hereinbelow.

In one example, the device has an at least partially transparent area, on which area the user has to position his finger before the device pricks the finger with a pricking mechanism (say with a lancet or a needle) that is a part of the device's sample taker, as described in further detail hereinbelow.

In the example, the camera is installed on the device, under the at least partially transparent area, and when the user positions his finger on the at least partially transparent area, the device automatically captures a picture of the finger with the image capturer (say camera), as described in further detail hereinbelow.

Optionally, apparatus 1000 further includes an image receiver, in communication with the image capturer.

The image receiver receives the image of the body part (say finger) captured by the image capturer, and stores the received image on a computer memory, say on a temporary memory (say on RAM (Random Access Memory)), as known in the art.

Optionally, apparatus 1000 further includes an image analyzer, in communication with the image receiver.

The image analyzer analyses the captured image, say using image processing techniques, say for identifying pricks on the finger, for counting the number of pricks present on the finger, for identifying traces of blood (say blood stains) on the finger, etc., or any combination thereof, as described in further detail hereinbelow.

In one example, the pricks or blood stains may be identified using feature detection techniques that typically involve steps such as localization—in which a location of each specific feature (say an object such as a prick, a blood stain, etc.) appearing on the finger as captured in the image, is found in the image.

The location may be found, for example, using a blob detection technique such as PCBR (Principal Curvature-based Region Detector), Grey Level Blob Detection Techniques such as Lindberg's scale space based methods, MSER (Maximally Stable External Regions), etc., as known in the art.

The feature detection techniques may also involve other steps, say a step of classification in which step, the feature (say a prick or a blood stain) is identified using classification methods (say Viola-Jones based methods, Support Vector Machines (SVM) based methods, etc., as known in the field of objects detection).

In the analysis, the image analyzer may further identify one or more finger areas that are better suited for taking the sample (say an area where no pricks are found), finger areas that are not suited for taking the sample (say an area in which the number of pricks exceeds a threshold predefined by a programmer of the apparatus 1000), etc., as described in further detail hereinbelow.

Additionally or alternatively, as a part of the analysis, the image analyzer may determine whether the user should rather take the fluid sample from another one of the user's fingers.

For example, the image analyzer may determine that the user should take the sample from another finger when the finger is over-pricked (say when the number of pricks identified on the finger in the analysis of the captured image exceeds a threshold predefined by a programmer of a computer the apparatus 1000). The image analyzer may similarly determine that the user should take the sample from another finger when the finger is covered with one or more blood stains that may be indicative of fresh bleeding from a wound, etc., as described in further detail hereinbelow.

Optionally, apparatus 1000 further includes a user guider, in communication with the image analyzer.

Based on the analyzed image, the user guider guides the user in taking the fluid sample, say using messages presented on a small (say LCD (Liquid Crystal Display)) screen that may be installed on the device, using vocal instructions given to the user using one or more speakers that may be installed on the device, etc.

Thus, in one example, the user may be advised by the user guider, to take the fluid sample from another one of his fingers since the finger is over-pricked, as described in further detail hereinabove.

The user may thus be guided to take the sample from another finger, for example, when the number of pricks identified on the finger in the analysis of the captured image exceeds the predefined threshold, when the finger has some areas that are covered with traces of blood (say blood stains), which may be indicative of fresh bleeding from previous pricking, etc.

In a second example, the user may be asked to change the orientation of his finger when positioned on the device, so as to allow the device to prick the finger at one of the areas of the finger determined to be better suited for taking the fluid, etc., as described in further detail hereinbelow.

After the user changes the finger's orientation or positions another finger on the device, the image capturer (say camera) is automatically (say using a weight based mechanism) or manually (say using a dedicated bottom) triggered to capture a new image (i.e. an image of the other finger or of the old finger in the new orientation), as described in further detail hereinbelow.

Then, the new image is similarly analyzed by the image analyzer.

If the analysis of the new image indicates that the number of pricks (if any) appearing on the finger is below the predefined threshold and that no blood traces appear to be present on the finger, the user guider advises the user that the body part is ready to be pricked for taking the fluid sample. The user guider may advise the user that body part is ready for pricking, using messages presented on the screen, using vocal instructions given to the user using the speakers, etc., as described in detail hereinbelow.

Optionally, in the exemplary embodiment, on the device used to take the fluid sample, there is alternatively or additionally measured an electric property of the fluid sample (say a one indicative of pH of the sample) taken from the body part, an optical property of the taken fluid sample (say a one indicative of hemoglobin content of the sample), etc., as described in further detail hereinbelow.

Figure 2:
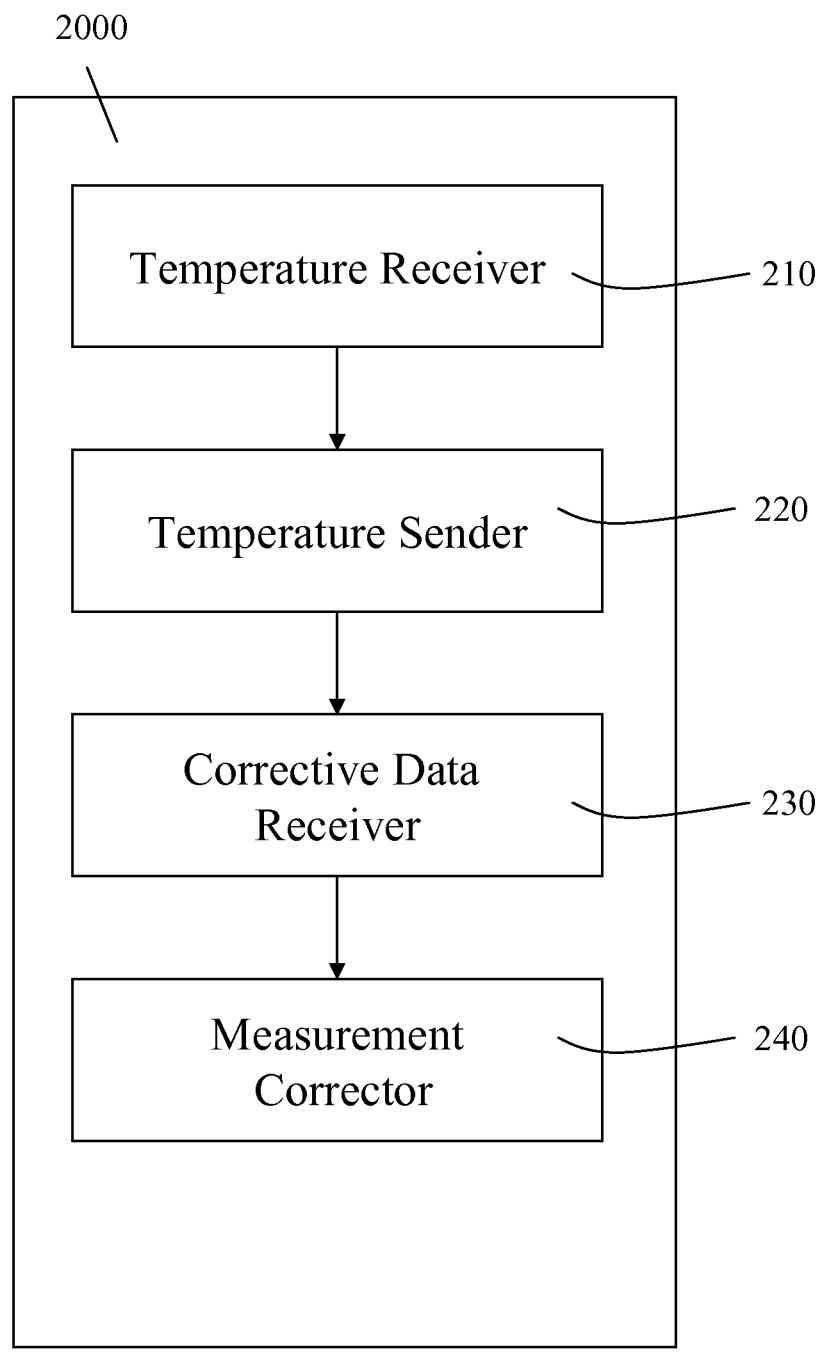
FIG. 2 is a simplified block diagram schematically illustrating a second exemplary apparatus for measuring body fluid content, according to an exemplary embodiment of the present invention.

Reference is now made to FIG. 2, which is a simplified block diagram schematically illustrating a second exemplary apparatus for measuring body fluid content, according to an exemplary embodiment of the present invention.

Apparatus 2000 for measuring body fluid content may be implemented using electric circuits, computer software, computer hardware, other components, etc., as described in further detail hereinbelow.

Optionally, the apparatus 2000 is implemented on a computer processor of a device used to take fluid samples from subjects (say persons, pets, farm animals, etc.), say on the device described in further detail hereinbelow and illustrated using FIG. 3.

Optionally, the apparatus 2000 is rather implemented on a computer processor of a computer coupled to the device, of a computer that is in communication with the device (say over a short ranged connection such as a local Area Network or a Wi-Fi Connection), etc., as described in further detail hereinbelow.

Optionally, the apparatus is implemented on both the device and the computer coupled to the device, or on both the device and the computer in communication with the device—say with some parts of the apparatus 2000 being implemented on the device, and some parts of the apparatus 2000 being implemented on the computer, or rather on the device and both computers.

The apparatus 2000 thus includes a computer processor.

The apparatus 2000 further includes one or more additional parts, as described in further detail hereinbelow, such as the parts 210-240 shown in FIG. 2, and described in further detail hereinbelow.

The additional parts may be implemented as software—say by programming the computer processor to execute the steps of the method described in further detail and illustrated using FIG. 5 hereinbelow, as hardware—say as an electric circuit that implements at least a part of that method, etc., or any combination thereof.

The apparatus 2000 includes a temperature receiver 210, implemented on the Computer processor.

The temperature receiver 210 receives a measured temperature value of a body part of a subject, say a temperature measured by a part of the device used to take the fluid sample when taking the sample or by a device used concurrently therewith, as described in further detail hereinbelow.

The apparatus 2000 further includes a temperature sender 220, in communication with the temperature receiver 210.

The temperature sender 220 sends the measured temperature value received from the temperature receiver 210, to a computer in communication with the apparatus 2000, say to apparatus 1000, as described in further detail hereinabove.

The apparatus 2000 further includes a corrective data receiver 230, implemented on the computer processor.

The corrective data receiver 230 receives corrective data that is generated on the computer in communication with the apparatus 2000 based at least on the sent temperature value and on data previously gathered on that computer in communication with apparatus 2000, from that computer (say from apparatus 1000), as described in further detail hereinabove.

The apparatus 2000 further includes a measurement corrector 240, in communication with the corrective data receiver 230.

The measurement corrector 240 corrects a measurement of content of the fluid sample taken by the device, using the corrective data received by the corrective data receiver 230, as described in further detail hereinbelow.

In a first example, the corrective data defines a function to be applied on the result of the measurement, for correcting the result, say by replacing the result with a corrected value, with a range of corrected values, with a value closest to the result but still within that range, etc., as described in further detail hereinbelow.

In a second example, the temperature sender 220 further sends a result of the measurement of the fluid sample to apparatus 1000, together with the measured temperature value of the body part.

In the second example, the corrective data includes the corrected result itself, say a corrected value to replace the result with, a range of values to replace the result with, a range of value to be used for replacing the result by choosing a value closest to the result but within the range, etc., as described in further detail hereinbelow.

Optionally, the apparatus 2000 further includes a temperature meter—say a thermometer installed on the device used to take the sample or on the device used concurrently therewith, and a temperature measurer that is implemented on the computer processor and is in communication with the temperature receiver 210.

The temperature measurer measures the value of the temperature of the body part of a subject, using the temperature meter, as described in further detail hereinbelow.

In one example, the temperature meter is installed on the device used to take the fluid sample, and is adapted for measuring the temperature of the body part while the device is being used to take the fluid sample from the body part, as described in further detail hereinbelow.

In the example, the temperature measurer is implemented on the computer processor of the device used to take the fluid sample from the body part of the subject, and the temperature measurer measures the value of a temperature of the body part using the temperature meter, as described in further detail hereinbelow.

Optionally, the apparatus 2000 further includes a sample taker—say a one made of a blood drawing component (say a one with a lancet or needle used to prick the body part), one or more tubes, one or more storage compartments (say vials, miniature compartments of a Lab-on-a-Chip (LOC), etc.). The blood drawing component may further include one or more pumps (say a pump that is operable by a user or a pump triggered automatically), that is used for pumping the sample from the body part to the compartment, as described in further detail hereinbelow.

Optionally, the apparatus 2000 further includes a content measurer, in communication with the sample taker and the measurement corrector 240.

The content measurer measures the content of the sample, say the concentration of a specific pathogen in the fluid sample, and hence in the subject's body fluid (say the concentration of a specific parasite in the subject's blood), as described in further detail hereinbelow.

Optionally, the content measurer measures the content using DNA polymerization, using another chemical process, etc., as described in further detail hereinbelow.

Optionally, the apparatus 2000 further includes a temperature controller in communication with the temperature receiver 210.

The temperature controller changes the temperature of the body part into a predetermined value prior to taking the fluid sample from the body part using the device, as described in further detail hereinbelow, and as illustrated, for example using FIG. 3.

The temperature may be predefined by a user or programmer of apparatus 2000, as described in further detail hereinbelow.

Optionally, the apparatus 2000 further includes a biometry data taker, implemented on the computer processor.

The biometry data taker takes biometry data from the body part (say hand) that the fluid sample is taken from, say using a biometric data reader, say a fingerprint scanner installed on the device used to take the sample, as described in further detail hereinbelow.

The taken biometric data may be used for determining which samples belong to a same subject (say a same patient), say for selecting samples among previously taken sample, to be used for generating the corrective data from, as described in further detail hereinbelow.

Optionally, the device used to take the fluid sample further includes an image capturer, say a scanner or a camera used to capture an image of the body part (say the user's finger, upper arm part, etc.) prior to the taking of the fluid sample from that body part, as described in further detail hereinbelow.

Optionally, the image capturer is automatically (say using a weight based mechanism) or manually (say using a dedicated bottom) triggered to capture the image, as described in further detail hereinbelow.

Optionally, apparatus 2000 further includes an image receiver, in communication with the image capturer of the apparatus used to take the body fluid sample.

The image receiver receives the image of the body part (say finger) as captured by the image capturer, and stores the received image on a computer memory, say on a temporary memory (say on RAM (Random Access Memory)), as described in further detail hereinbelow.

Optionally, apparatus 2000 further includes an image analyzer, in communication with the image receiver.

The image analyzer analyses the received image, say using image processing techniques, say for identifying pricks on the finger, for counting the number of pricks present on the finger, for identifying traces of blood (say blood stains) on the finger, etc., or any combination thereof, as described in further detail hereinabove.

In the analysis, the image analyzer may further identify finger areas that are better suited for taking the sample (say an area where no pricks are found), finger areas that are not suited for taking the sample (say an area in which the number of pricks exceeds a threshold predefined by a programmer of the apparatus 2000), etc., as described in further detail hereinabove.

Additionally or alternatively, as a part of the analysis, the image analyzer may determine whether the user should rather take the sample from another one of the user's fingers—say when the finger is over-pricked (say when the number of pricks identified on the finger in the analysis of the captured image exceeds a threshold predefined by a programmer of a computer the apparatus 2000), etc., as described in further detail hereinabove.

Optionally, apparatus 2000 further includes a user guider, in communication with the image analyzer.

Based on the analyzed image, the user guider guides the user in taking the fluid sample, say using messages presented on a small (say LCD (Liquid Crystal Display)) screen that may be installed on the device, using vocal instructions given to the user using one or more speakers that may be installed on the device, etc., as described in further detail hereinabove.

For example, the user may be advised by the user guider, to take the fluid sample from another one of his fingers since the finger is over-pricked, to change the orientation of his finger when positioned on the device, so as to allow the device to prick the finger at one of the areas of the finger—the area determined to be better suited for taking the sample from, etc., as described in further detail hereinabove.

After the user changes the finger's orientation or positions another finger on the device, the image capturer (say camera) is automatically (say using a weight based mechanism) or manually (say using a dedicated bottom) triggered to capture a new image (i.e. an image of the other finger or of the old finger in the new orientation).

Then, the new image is similarly analyzed by the image analyzer, and if the analysis of the new image indicates that the number of pricks (if any) appearing on the finger is below the predefined threshold and that no blood traces appear to be present on the finger, the user guider advises the user that the finger is ready to be pricked for taking the fluid sample, as described in further detail hereinbelow.

Figure 3:
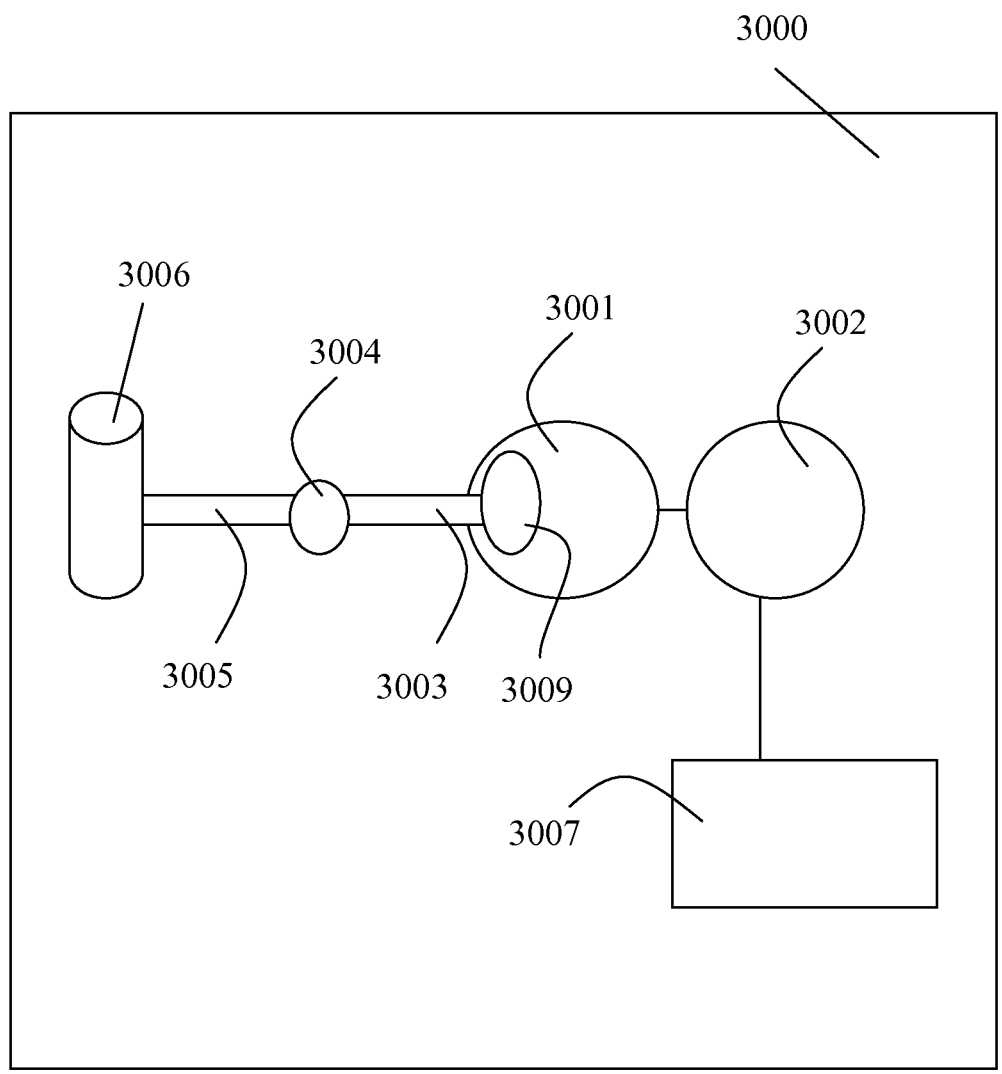
FIG. 3 is a simplified block diagram schematically illustrating a third exemplary apparatus for measuring body fluid content, according to an exemplary embodiment of the present invention.

Reference is now made to FIG. 3, which is a simplified block diagram schematically illustrating a third exemplary apparatus for measuring body fluid content, according to an exemplary embodiment of the present invention.

Apparatus 3000 for measuring body fluid content may be implemented using electric circuits, computer software, computer hardware, one or more temperature meters, a Lab-on-Chip (LOC), other components, etc., or any combination thereof, as described in further detail hereinbelow.

Optionally, some parts of the apparatus 3000 are implemented on a computer processor of a device used to take fluid samples from subjects (say persons, pets, farm animals, etc), whereas other parts of the apparatus 3000 are implemented on other components of the device.

The apparatus 3000 may thus include a computer processor 3007 and a computer memory (say a Flash Memory or an SSD Drive), implemented on a device used for taking a fluid sample from a subject, as described in further detail hereinbelow.

Optionally, the apparatus 3000 further includes a surface 3001 on which a body part (say a finger) of a subject (say a patient) is placed, say a piece of metal installed on a bottom of an elongated depression formed into a side of the device, wherein the depression is designed for a human finger to be positioned in, as known in the art.

Optionally, the surface 3001 is rather an at least partially transparent area, say an at least partially transparent plastic surface that makes up the bottom of the elongated depression formed into a side of the device, and the apparatus 3000 further includes an image capturer (say a camera) that is installed under the plastic surface, as described in further detail hereinabove.

The image capturer is in communication with the computer processor 3007, say for forwarding the captured image (i.e. image data) to an image receiver implemented on the computer processor 3007, as described in further detail hereinabove.

The image capturer may be, for example, a scanner or a camera used to capture an image of the body part (say the user's finger) prior to the taking of the fluid sample from that body part, as described in further detail hereinbelow. The camera may be a visible light camera, an IR (Infra Red) Camera, etc., as known in the art.

In one example, the user has to position his finger on the at least partially transparent area before the apparatus 3000 pricks the finger with a pricking mechanism (say a one with a needle) that is a part of the device's sample taker, as described in further detail hereinbelow.

Optionally, in the example, when the user positions his finger on the at least partially transparent area, the image capturer (say camera) is automatically triggered to capture the image.

For example, a weight based sensor (say a pressure meter) may be installed under a part of the plastic surface and be connected to the image camera in an electric circuit, such that when the user positions a finger on the surface, the weight based sensor senses the weight applied to the surface by the finger. Upon the sensing of the weight applied to the surface, the weight based sensor triggers the camera to capture an image of the finger, as described in further detail hereinbelow.

The apparatus 3000 may further include a temperature measurer implemented on the computer processor 3007 and a temperature meter (say thermometer) 3002 connected to the surface 3001, as described in further detail hereinabove.

When the subject places his body part (say finger) on the surface 3001, inside the depression, the temperature measurer measures the temperature of the subject's body part (say finger), using the temperature meter 3002, as described in further detail hereinabove.

Optionally, the temperature measurer further uses the temperature meter 3002 (or rather a second temperature meter) to measure ambient temperature when the subject's finger is inside the depression, on the surface 3001, or rather immediately before or after to the subject's places his finger inside the depression.

The temperature measurer stores the measured temperature value(s) in the computer memory, on the device.

The exemplary apparatus 3000 may further include a sample taker—say a one made of a blood drawing component—say a one with a lancet 3009 or needle 3009 used to prick the body part installed on a side of the depression, one or more tubes 3003, 3005, one or more storage compartments (say vials) 3006 and one or more pumps 3004.

For example, the apparatus 3000 may include a lancet 3009 used to prick a finger placed in the depression, a LOC (Lab-on-Chip) connected to the depression's bottom with a tube 3003, 3005, and a miniature mechanical pump 3004 used to pump blood from the bottom of the depression into compartments 3006 inside the LOC, as known in the art.

When operated by a user (say using an actuating mechanism connected to the lancet and the pump, as known in the art), the lancet 3009 is pushed so as to prick the side of the finger, and the pump pumps blood from the bottom of depression to the storage compartment(s) 3006, through the tubes 3003, 3005.

Optionally, apparatus 3000 further includes an image receiver, implemented on the computer processor 3007. The image receiver is in communication with the image capturer, as described in further detail hereinabove.

The image receiver receives the image of the body part (say finger) as captured by the image capturer, and stores the image on a computer memory, say on the computer memory, as described in further detail hereinabove.

Optionally, apparatus 3000 further includes an image analyzer, implemented on the computer processor 3007. The image analyzer is in communication with the image receiver, as described in further detail hereinabove.

The image analyzer analyses the captured image, say using image processing techniques, say for identifying pricks on the finger, for counting the number of pricks present on the finger, for identifying traces of blood on the finger, etc., or any combination thereof, as described in further detail hereinbelow.

In one example, the pricks and blood traces (say a blood stain) may be identified using feature detection techniques that typically involve steps such as localization—in which a location of each specific feature (say an object such as a prick or a stain of blood) appearing on the finger as captured in the image, is found in the image. The feature may be found, for example, using a blob detection technique such as PCBR (Principal Curvature-based Region Detector), Grey Level Blob Detection Techniques such as Lindberg's scale space based methods, MSER (Maximally Stable External Regions), etc., as known in the art.

The feature detection techniques may also involve other steps, say a step of classification, in which step, the feature (say a prick or a blood stain) is identified using classification methods (say Viola-Jones based methods, Support Vector Machines (SVM) based methods, etc., as known in the field of objects detection).

In the analysis, the image analyzer may further identify one of more areas of the finger that are better suited for taking the sample (say an area where no pricks are found), finger areas that are not suited for taking the sample (say an area in which the number of pricks exceeds a threshold predefined by a programmer of the apparatus 3000), etc., as described in further detail hereinabove.

Additionally or alternatively, as a part of the analysis, the image analyzer may determine whether the user should rather take the sample from another one of the user's fingers—say when the finger is over-pricked (say when the number of pricks identified on the finger in the analysis of the captured image exceeds a threshold predefined by a programmer of a computer the apparatus 3000), etc., as described in further detail hereinbelow.

Optionally, apparatus 3000 further includes a user guider, implemented on the computer processor 3007. The user guider is in communication with the image analyzer.

Based on the analyzed image, the user guider guides the user in taking the fluid sample, say using messages presented on a small (say LCD (Liquid Crystal Display)) screen that may be installed on the device, using vocal instructions given to the user using a speaker that may be installed on the device, etc.

Thus, in one example, the user may be advised by the user guider, to take the fluid sample from another one of his fingers since the finger is over-pricked, as described in further detail hereinabove.

The user may be guided to take the sample from another finger, for example, when the number of pricks identified on the finger in the analysis of the captured image exceeds the predefined threshold, when the finger has some areas that are covered with traces of blood (say blood stains), which may be indicative of fresh bleeding from previous pricking, etc.

In a second example, the user guider may ask the user to change the orientation of his finger when positioned on the device, so as to allow the device to prick the finger at the area of the finger determined to be better suited for taking the fluid, etc., as described in further detail hereinabove.

After the user changes the finger's orientation or positions another finger on the device, the image capturer (say camera) is automatically (say using a weight based mechanism) or manually (say using a dedicated bottom) triggered to capture a new image (i.e. an image of the other finger or of the old finger in the new orientation), as described in further detail hereinabove.

Then, the new image is received by the image receiver and is similarly analyzed by the image analyzer.

If the analysis of the new image indicates that the number of pricks (if any) appearing on the finger is below the predefined threshold and no blood traces appear to be present on the finger, the user guider advises the user that the finger is ready to be pricked for taking the fluid sample. The user guider advises the user using a speaker, an LCD screen, etc., as described in further detail hereinabove.

The apparatus 3000 may further include a content measurer, as described in further detail hereinabove, implemented on the computer processor 3007.

The content measurer measures the content of the fluid (say blood) sample, say the concentration of a specific pathogen in the fluid sample, and hence in the subject's body fluid (say the concentration of a specific parasite in the subject's blood), as described in further detail hereinbelow.

Optionally, the content measurer measures the concentration of the pathogen using a chemical process such as a DNA polymerization based chain process (say PCR) carried out in the compartment(s) 3006, say in a Lab-on-a-Chip (LOC) micro-fluidic chip, as described in further detail hereinabove.

In one example, the process uses Y-shaped molecules, as described in further detail hereinabove.

Each Y-shaped molecule has a single-stranded DNA or an antibody attached to the Y-shaped molecule's base and designed to pair with complementary DNA of a specific pathogen. The Y-shaped molecule further has a molecule attached to one of the upper arms of the Y-shaped molecule that chains up with similar molecules when exposed to ultraviolet (UV) light, as described in further detail hereinabove.

In the example, The Y-shaped molecules are added in advance to the compartment(s) 3006, and lock onto the pathogen if present in the taken sample.

In the example, the apparatus 3000 further includes an ultraviolet (UV) light source installed on the device, next to the compartment(s) 3006, and a fluorescence reader, as known in the art.

When UV light is emitted from the light source installed on the device, the Y-shaped molecules, if paired with the pathogen's DNA, link to form long chains of Y-molecules, as described in further detail hereinabove.

As a result, with the pathogen present in the fluid sample and the UV light emitted from the light source, a resulting chain reaction is easily detected in the compartment, and omits fluorescence in a level that may be measured by the fluorescence reader.

The fluorescence level measured by the fluorescence reader is then used by the content measurer, to assess the pathogen's concentration in the fluid sample.

The content measurer stores the measured content's value in the computer memory, in associated with the measured value of body part's temperature value, the measured ambient temperature value, or both.

Alternatively or additionally, the content measurer may measure an electric property of the fluid sample (say a one indicative of pH of the sample) taken from the body part—say using electrodes installed in one or more of the compartment(s) 3006, etc., as known in the art.

Alternatively or additionally, the content measurer may measure an optical property of the taken fluid sample (say a one indicative of hemoglobin content of the sample)—say using a miniature camera or electro-optical sensor installed above, below or beside one or more of the compartment(s) 3006, etc., as known in the art. In one example, the apparatus 3000 further includes a biometric data reader—say a fingerprint scanner similar to the ones used on finger print readers and on some laptop computers. In the example, the biometric data reader is installed on the device, say on the bottom of the depression (say for taking a fingerprint image of the finger) or rather on an area on which another one of the subject's fingers rests during the sample's taking (say for taking a fingerprint image of the other finger).

In the example, the apparatus 3000 further includes a biometry data taker, implemented on the computer processor 3007.

The biometry data taker takes biometry data from the body part (say hand) that the fluid sample is taken from, using the biometric data reader, and stores the biometry data in the memory, as described in further detail hereinabove.

The taken biometric data may be used for determining which samples belong to a same subject (say a same patient), say by the computer in communication with the device used to take the sample, as described in further detail hereinabove. For example, the computer may use the biometry data for selecting samples among previously taken sample, to be used for generating the corrective data from, as described in further detail hereinabove.

Optionally, the apparatus' 3000 parts implemented on the computer processor 3007 are a part of apparatus 2000 or rather of apparatus 1000, in which case, one or more of the remaining parts of the apparatus 2000 or 3000, may also be implemented on the device's computer processor 3007, as described in further detail hereinabove.

In a first example, the apparatus 3000 includes, for example, the temperature receiver 210 of apparatus 2000 that in the first example, receives the measured temperature from the temperature measurer directly, or rather reads the temperature measured by the temperature measurer from the memory. In the first example, the apparatus 3000 further includes apparatus 2000's temperature sender 220, corrective data receiver 230, and measurement corrector 240, as described in further detail hereinabove.

In a second example, the apparatus 3000 includes, for example, the temperature receiver 110 of apparatus 1000 that in the second example, receives the measured temperature from the temperature measurer directly, or rather reads the temperature measured by the temperature measurer from the memory. In the second example, the apparatus 3000 further includes apparatus 1000's corrective data generator 120 and measurement corrector, as described in further detail hereinabove.

In one example, the apparatus 3000 further includes a thermoelectric cooler (TEC), a heating element, other known in art component capable of warming or cooling a surface when attached to the surface or installed in proximity thereto, etc., or any combination thereof, as known in the art.

The TEC, heating element or both, may by installed, for example, in the bottom or side of the depression designed for the subject to place his body part (say finger) in, beside the depression, etc., as known in the art.

In the example, the apparatus 3000 further includes a temperature controller implemented on the computer processor 3007, as described in further detail hereinabove.

The temperature controller controls the temperature of the body part (say finger), say by cooling or warming the body part prior to taking of the fluid sample from the body part by the device, by controlling the thermoelectric cooler (TEC), heating element, other component, etc., as described in further detail hereinabove.

Optionally, using the TEC, heating element, or other component, the temperature controller changes the temperature of the body part into a predetermined value prior to taking the fluid sample from the body part using the device, as described in further detail hereinabove.

The temperature may be predefined by a user or programmer of apparatus 3000, as described in further detail hereinbelow.

Figure 4:
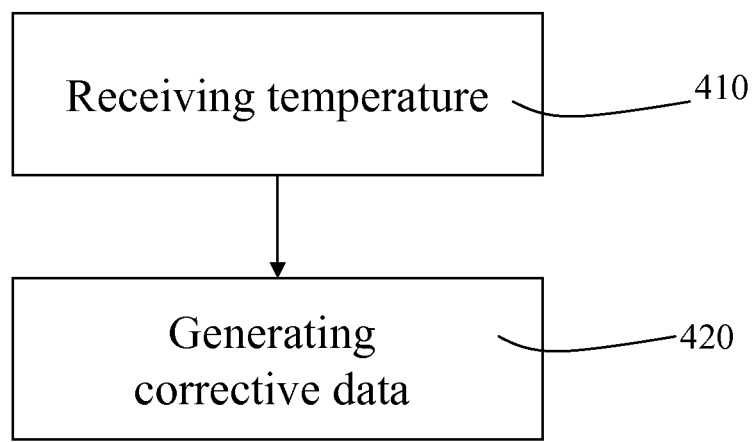
FIG. 4 is a simplified flowchart schematically illustrating a first exemplary method of measuring body fluid content, according to an exemplary embodiment of the present invention.

Reference is now made to FIG. 4, which is a simplified flowchart schematically illustrating a first exemplary method of measuring body fluid content, according to an exemplary embodiment of the present invention.

A first exemplary method for measuring body fluid content may be implemented using electric circuits, computer instructions, etc.

Optionally, the method is executed by a computer processor of a device used to take fluid (say blood) samples from subjects (say persons, animals, etc.), say by apparatus 1000, as described in further detail hereinabove.

Often, such a device is further used to measure a content of the taken sample, say by measuring a quantitative level (say concentration) of a pathogen (say a virus, bacteria, or protozoa), sugar, immune system components, etc., in the subject's blood or other body fluid, as described in further detail hereinabove.

The content may be measured using a chemical process, a measurement of an electric property of the sample (say a one indicative of pH of the sample) taken from the body part, an optical property of the taken sample (say a one indicative of hemoglobin content of the sample), etc., as described in further detail hereinabove.

Optionally, the method is rather implemented on a computer in communication with the device used to take the fluid samples, say on a server computer, as described in further detail hereinabove. The communication may be remote (say a communication over the internet), short ranged (say a communication over a wired LAN (local Area network) or over a Wi-Fi Connection), etc., as described in further detail hereinbelow.

In the method, there is received 410 a measured value of a temperature of a body part of a subject, say a temperature value measured by a device used to take a fluid sample from the body part (say to take blood from a finger—i.e. from one of the finger's narrow capillaries) or by a device (say thermometer) used concurrently therewith. The measured temperature value may be received 410, for example, by the temperature receiver 110 of apparatus 1000, as described in further detail hereinabove.

Optionally, with the value of a temperature of the subject's body part, there is additionally or alternatively received 410 one or more additional parameters, say an ambient temperature value measured by the device when taking the sample or the by the device used concurrently therewith, etc. Possibly, with the measured temperature value, there is further received 410 by the temperature receiver 110, a measurement of a content of the sample (i.e. a measured value), to be corrected, as described in further detail hereinabove.

The temperature receiver 110 may be implemented on the device, on a computer in communication with the device, etc., as described in further detail hereinabove.

Thus, in a first example, the temperature value is received 410 on the device, from one of the parts of the device, whereas in a second example, the temperature value is received 410 on the computer in communication with the device, from the device, as described in further detail hereinabove.

Next, there is generated 420 corrective data (say data defining a function having one or more parameters) based on the received 410 temperature value and on previously gathered data, say by the corrective data generator 120, as described in further detail hereinabove.

Optionally, the corrective data's generation 420 is further based on one or more of the additional parameters received 410 with the body part's temperature value, as described in further detail hereinbelow.

The corrective data is usable for correcting a measurement of content of the fluid sample taken by the device, as described in further detail hereinabove.

In one example, the fluid sample is taken by the device, the sample's content is measured by the device, and the measurement of the content is corrected by the device (say by the measurement corrector) based on the corrective data. In the example, the corrective data is also generated by the device (say by the corrective data generator), as described in further detail hereinabove.

In a second example too, the fluid sample is taken by the device, the sample's content is measured by the device, and the measurement of the content is corrected by the device (say by the measurement corrector) based on the corrective data.

However, in the second example, the corrective data is generated by the computer in communication with the device (say by the corrective data generator) and sent from the computer to the device, as described in further detail hereinabove.

In a third example, the fluid (say blood) sample is taken by the device and the sample's content is measured by the device.

However, in the third example, the device sends that measurement's result to the computer in communication therewith, and the measurement is corrected by the computer based on the corrective data generated by the computer (say by the measurement corrector), by correcting the result, as described in further detail hereinabove.

Optionally, in the method, the measurement is corrected by replacing the measurement's result value with a value, with range of values, etc., as described in further detail hereinbelow.

In a first example, the generated 420 corrective data defines a function that when applied to the measurement's result (say by the measurement corrector), yields a range of values, as described in further detail hereinabove.

In the first example, the measurement is corrected using the corrective data whenever a result of the measurement is not within that range of values based on the generated 420 corrective data, say by replacing the result with a value closest to the result but still within that range, as described in further detail hereinbelow.

In a second example too, the corrective data defines a function that when applied to the measurement's result, yields a range of values. However, in the second example, the result is always replaced with the value range based on the corrective data, as described in further detail hereinbelow.

Optionally, the previously gathered data that is used for generating the corrective data includes data on two or more previously taken fluid (say blood) test samples, as described in further detail hereinabove.

Optionally, the data on the previously taken test samples is used to follow several subjects' (say patients') disease progresses.

In one example, for each one of the samples, the data on the test sample includes biometric data usable for determining which of the test samples belong to a same subject, the type of measurement carried out on the sample, an indication on the subject's disease stage, etc., or any combination thereof.

More specifically, in the example, the data on the previously taken samples includes for each one of the samples, at least two parameters—namely, a respective measured temperature value of a body part as measured when taking the test sample from the body part and a respective content value measured using the test sample.

Optionally, for each one of the previously taken samples, the data further includes one or more additional parameters.

The additional parameters may include, but are not limited to: a time indication (say a time of taking of the respective sample, whether absolute or relative to a start of a series made of at least some of the test samples), a disease stage indication, an ambient temperature value measured when taking the test sample, etc., or any combination thereof.

The parameters may also include, an alternative measurement value (say a one obtained using a device different from a device used to take the test sample), a light reading (say for assessing blood oxygen saturation of the sample), hemoglobin level, a temperature of a body part other than the one that the test sample is taken from, the subject's blood pressure, etc.

Optionally, the parameters received for the test samples, are historic values gathered by the device or received by the computer from the device, from similar devices, or from both, as described in further detail hereinbelow.

In a first example, the corrective data defines a function that when applied on the parameters, yields a corrected value and an expected error.

Optionally, the corrected value and the expected error define a range of values that should replace the measurement's result.

Alternatively, the corrected value and the expected error define a reference normal range. When the result deviates from the reference normal range, the result is replaced by the maximal value or rather with the minimal value within that range, and more specifically, with a value that is closest to the result, but is still within the range, as described in further detail hereinabove.

In the first example, the function is calculated by multiparametric fitting as known in the art, say by the corrective data generator 120, as described in further detail hereinabove.

Optionally, the fitting is based on a Neuronal Network that provides a function correlating between a series of tuples in which each tuple includes the parameters received for a respective one of the test samples, and a target correction tuple that includes the corrected value and the expected error, as known in the art.

Optionally, the fitting is based on a non-linear manifold learning method, such as Diffusing Mapping, and an extraction of a multivariate out-of-sample extension function from the Diffusing Mapping. The out-of-sample extension function is used to estimate a weighting of the different parameters for each tuple, etc., as known in the art.

Optionally, the function to be applied on the parameters (i.e. the corrective data) is a part of data that is predefined arbitrarily (say by an administrator or programmer of apparatus 1000).

Thus, in one example, an administrator of apparatus 1000 defines a table that maps body part temperatures (possibly, with one or more other parameters) into corrective data such as a factor that the measurement's result needs to be multiplied by or a mathematical function to be applied to the measurement's result, in order to yield the corrected result.

In a second example, the administrator defines a preliminary arbitrary model for the relationship among the different parameter using an exemplary equation such as:

$$Qm = a + b \times Qr + c \times Ta + d \times Tf^2$$

In the example, Qm—denotes the result of a measured concentration of a content (say pathogen) of the fluid sample taken from the subject by the device, and Qr—denotes the real concentration of the content in the subject's blood—i.e. the value that the measurement should to be corrected to. Further, Ta—denotes the ambient temperature measured by the device, and Tf—denotes the temperature of the body part (say finger) that the sample is taken from.

In the example, the administrator sets the value of b and c arbitrarily (say according to known scientific literature) to 2 and 4, respectively. However, the values of a and d are determined automatically, say by the corrective data generator 120, as described in further detail hereinabove.

Specifically, in the example, the values of a and d are determined automatically based on the data on the test samples—i.e. the fluid samples previously taken from the same subject during a short time period (say of one hour), as a part of calculating the function for the corrective data to define.

More specifically, the values of a and d are calculated by resolving a system of equations, where each equation is created using the parameters received for a specific one of the subject's test samples during that short time period. Further, the real concentration of the content in the subject's blood (Qr) is assumed to be constant for that short time period.

Thus, in the example, when the parameters received for one of the test samples during the short time period includes a finger temperature (Tf) of 29 degrees, an ambient temperature (Ta) of 24 degrees, and a measured concentration (Qm) of 110 microgram/liter, the resultant equation for that test sample is:

$$110 = a + 2 \times Qr + 4 \times 24 + d \times 29^2$$

Similarly, when the parameters received for a second one of the subject's test samples of that short time period includes a finger temperature (Tf) of 30 degrees, an ambient temperature (Ta) of 25 degrees, and a measured concentration (Qm) of 121 microgram/liter, the resultant equation for that test sample is:

$$121 = a + 2 \times Qr + 4 \times 25 + d \times 30^2$$

When the parameters received for a third one of the subject's test samples of that short time period includes a finger temperature (Tf) of 35 degrees, an ambient temperature (Ta) of 32 degrees, and a measured concentration (Qm) of 190 microgram/liter, the resultant equation for that test sample is:

$$190 = a + 2 \times Qr + 4 \times 26 + d \times 35^2$$

By solving an equation system made of the three equations, the values of a and d can be calculated, thus yielding a function, that in this example, is a more specific version of the administrator's exemplary equation (namely, a one in which a, b, c, and d are of known constant values).

If the previously gathered data (i.e. the parameters received for the test samples) does not include enough data (say when the number of equations that can be calculated based on parameters received for a same subject during a same short period of say one hour, is not enough to solve such an equation system), simulated data may need to be added.

For example, in previous example, if the number of equations would not be enough, the simulated data could include parameters calculated by averaging between the parameters gathered for the subject during that same short time period (say by generating a simulated set of parameters where Tf=(29+30+35)/3 and Ta=(24+25+26)/3.

Alternatively, the missing data may be simulated using an extrapolation method run on the parameters received for that subject for other periods, for test samples (i.e. previous fluid samples) taken from other subjects, etc., as known in the art.

After the function is calculated that way, corrective data that defines the function may be used for correcting a measurement of content of a sample taken from the specific subject, based on ambient temperature and finger temperature measured when taking the sample, since:

$$Qr = (Qm - a - c \times Ta - d \times Tf^2)/b$$

Additionally or alternatively, a function that is not subject-specific may be calculated and used in the corrective data, say by extrapolating over functions arrived at similarly for different subjects (say different patients).

Additionally or alternatively, the generation of the function may be further based on a fitting of the data (i.e. the parameters) received for the test samples to a disease progress model, say to a disease progress curve based on scientific literature data, as known in the art.

Potentially, with such fitting, variation in the temperature may be smoothed out, yielding a model with which received measured body part temperature, and possibly other parameters received with the measured temperature, may also help estimate the subject's disease stage.

The model may thus be used, say with the measured body part temperature, and possibly with other parameters received with the measured temperature, to estimate the subject's disease stage, as described in further detail hereinbelow.

Thus, optionally, in the method, there is further generated disease progress data (say an indication on a stage of a disease that the subject suffers from) based on the temperature value (and possibly, other parameters) received for a recently taken fluid sample, and the previously gathered data. The disease progress data may thus be generated, for example, using the result of the fitting to the disease progress model, say by the disease progress data generator of apparatus 1000.

The disease progress model may be calculated using a learning machine method, say a one similar to one or more of methods used to calculate the function that when applied on the parameters, yields the corrected value and the expected error, as described in further detail hereinabove.

Thus, in one example, a programmer or administrator of apparatus 1000 may define one or more tables, such that each one of the table maps different combinations of corrected values (i.e. corrected results), body part temperatures, etc., into a clinical stage of a specific disease that the value in the tables pertain to.

Thus, for example, the administrator may define a table that maps different combinations—wherein each combination includes a corrected result of pathogen content (say concentration) and a body part's temperature value—to a respective stage of the infection (say a latent stage, a non-terminal stage, a terminal stage, etc.).

In a second example, physicians provide several sets of disease progress stage estimation data. Each set includes data identifying the subject, a time of disease stage estimation, and an estimated stage (i.e. diagnosis).

Each of the sets further includes a set of sample data that pertains to samples taken by the subject within a number of hours (say six hours) before or after that time of disease stage estimate. The sample data includes for each one of one or more samples taken from the subject during those hours, a time of sample taking, and one or more parameters of the sample (say one or more of the parameters listed for test samples hereinabove).

In the example, the data provided by the physicians is used as a training set for generating a model that maps the parameters to estimated disease stages, say using a regression method (say linear regression) that yields a graph in a multi-dimensional space where each dimension represents one of the parameters, as known in the art.

The model generated based on the training set (i.e. the data provided by the physicians) that make up the previously gathered data of the example, may thus be used to generate disease progress data.

For example, the model (say graph) may be used to generate an indication on the subject's disease stage, based on a mapping of a measurement's result corrected using the corrective data and the temperature measured when taking the sample that the result pertains to, to that stage.

Optionally, in the method, there is further received (say by the temperature receiver 110) with the temperature value, biometric data, say biometric data taken by the device from the subject's body part, say fingerprint data taken from the subject's finger used to take the fluid sample from, as described in further detail hereinabove.

The biometric data may be used for determining which samples belong to a same subject.

Thus, in one example, the parameters received for each one of the test samples include an image of a fingerprint taken from the subject's finger when taking the test sample (say a blood sample) from the subject's finger.

In the example, there is selected one or more test samples to be used for generating 420 the corrective data (say data defining a function) from the previously gathered data (say by the corrective data generator 120), using the fingerprint data received for the sample subject to the measurement to be corrected, as described in further detail hereinabove.

In the method, after selecting the test samples using the fingerprint, there is generated 420 the corrective data based on the parameters received for the selected test samples— i.e. from fluid samples previously taken from a same subject as that of the sample for which the measurement is to be corrected using the corrective data.

The generation 420 of the corrective data is further based on the measured body part's temperature value (and possibly, other parameter values) received 410 for the sample for which the measured content value needs to be corrected, as described in further detail hereinabove.

Optionally, the method further includes changing the temperature of the body part prior to the taking of the fluid sample from the body part, say by controlling a thermoelectric cooler (TEC), a heating element, etc., installed on the device, as described in further detail hereinbelow.

In one example, the temperature is changed into a temperature value that is predefined by a programmer or operator of the device, or rather of the computer in communication with the device, as described in further detail hereinbelow.

Thus in the example, the body part is cooled or warmed into the predetermined temperature value prior to taking the fluid sample from the body part using the device. The warming or cooling of the subject's body part may further improve the accuracy of measurement of the content by the device, especially when the body part's temperature is pushed into a temperature range that may prove advantageous (say in as far as blood clotting, stickiness, etc., are concerned).

Optionally, in the method, there is further captured an image of the body part (say the user's finger, upper arm part, etc.) prior to the taking of the fluid sample from the body part, say using the image capturer (say a camera installed on the device), as described in further detail hereinabove.

Optionally, the captured image is then received—say by the image receiver of apparatus 1000, and is analyzed—say by the image analyzer of apparatus 1000, as described in further detail hereinabove.

Optionally, the image is analyzed, say using image processing techniques, say for identifying pricks on the finger, for counting the number of pricks present on the finger, for identifying traces of blood on the finger, etc., or any combination thereof, as described in further detail hereinabove.

In the analysis, there may be further identified one or more finger areas that are better suited for taking the sample (say an area where no pricks are found), one or more finger areas that are not suited for taking the sample (say an area in which the number of pricks exceeds a threshold predefined by a programmer of the apparatus 1000), etc., as described in further detail hereinabove.

Additionally or alternatively, as a part of the analysis, there may be determined whether the user should rather take the sample from another one of the user's fingers—say when the finger is over-pricked (say when the number of pricks identified on the finger in the analysis of the captured image exceeds a threshold predefined by a programmer of a computer the apparatus 1000), etc., as described in further detail hereinbelow.

Optionally, based on the analyzed image, the user is guided in taking the fluid sample, say by the user guider of apparatus 1000. The user may be guided using messages presented on a small (say LCD) screen, using vocal instructions given to the user using a speaker, etc., as described in further detail hereinabove.

Thus, in one example, the user may be advised by the user guider, to take the fluid sample from another one of his fingers since the finger is over-pricked, as described in further detail hereinbelow.

The user may be guided to take the sample from another finger, for example, when the number of pricks identified on the finger in the analysis of the captured image exceeds the predefined threshold, when the finger has some areas that are covered with traces of blood (say blood stains), which may be indicative of fresh bleeding from previous pricking, etc.

In a second example, the user may be asked to change the orientation of his finger when positioned on the device, so as to allow the device to prick the finger at the area of the finger determined to be better suited for taking the fluid, etc., as described in further detail hereinabove.

After the user changes the finger's orientation or positions another finger on the device, the image capturer (say camera) is automatically or rather, manually, triggered to capture a new image of the finger (i.e. an image of the other finger or of the old finger in the new orientation), as described in further detail hereinabove.

Then, the new image may be similarly analyzed, say by the image analyzer of apparatus 1000.

If the analysis of the new image indicates that the number of pricks (if any) appearing on the finger is below the predefined threshold and that no blood traces appear to be present on the finger, the user is advised that the body part is ready to be pricked for taking the fluid sample, say using the speakers or the screen, as described in further detail hereinabove.

Optionally, in the first exemplary method, there is alternatively or additionally measured an electric property of the fluid sample (say a one indicative of pH of the sample) taken from the body part, an optical property of the taken fluid sample (say a one indicative of hemoglobin content of the sample), etc., as described in further detail hereinabove.

Figure 5:
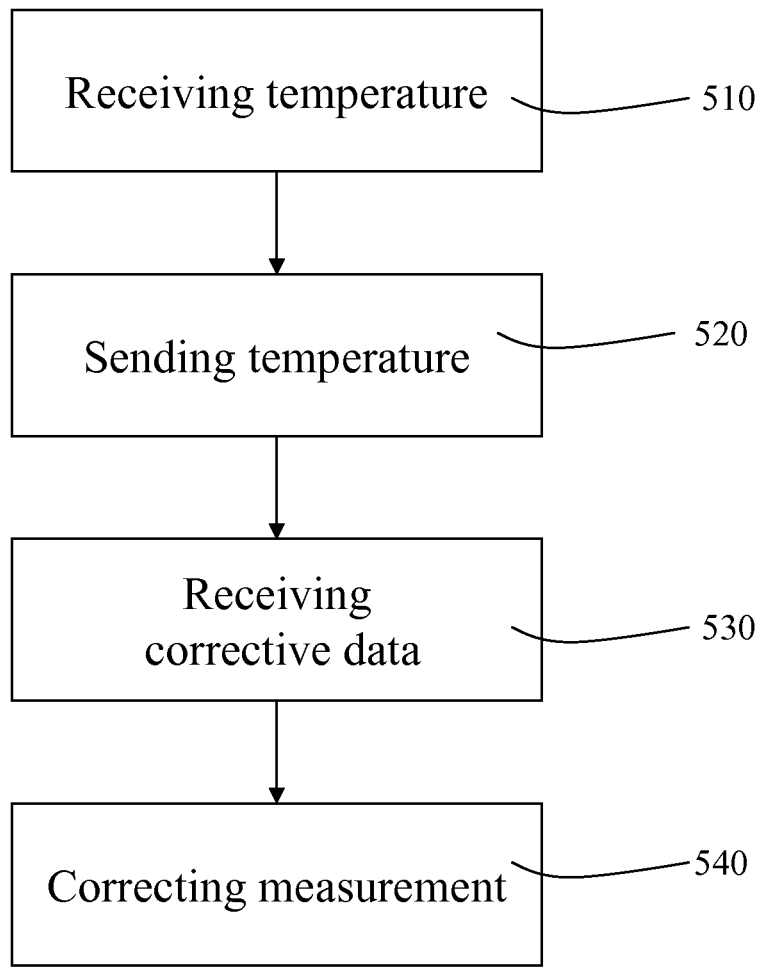
FIG. 5 is a simplified flowchart schematically illustrating a second exemplary method of measuring body fluid content, according to an exemplary embodiment of the present invention.

Reference is now made to FIG. 5, which is a simplified flowchart schematically illustrating a second exemplary method of measuring body fluid content, according to an exemplary embodiment of the present invention Optionally, the method is implemented on a computer processor of device used to take fluid (say blood) samples from subjects (say persons, animals, etc.), say by the device of the sort described in further detail hereinabove and illustrated using FIG. 3.

Often, the device is further used to measure a content of the taken sample, say to measure a quantitative level (say concentration) of a pathogen (say a virus, bacteria, or protozoa), sugar, immune system components, etc., in the subject's blood or other body fluid, as described in further detail hereinabove.

Optionally, the method is rather implemented on a computer processor of a computer coupled to the device, of a computer that is in communication with the device over a short ranged connection (say over a local Area Network or Wi-Fi Connection), etc., as described in further detail hereinabove.

Optionally, the method is implemented on both the device and the computer coupled to the device, on both the device and the computer in communication with the device—say by implementing some method steps on the device and some method steps on the computer, or on the device and both computers, as described in further detail hereinabove.

In the second exemplary method, there is received 510 a measured temperature value of a body part of a subject, say a temperature measured by the device used to take the fluid sample or by a device used concurrently therewith, when taking the sample, as described in further detail hereinabove. Optionally, the measured temperature value is received 510 by the temperature receiver 210 of apparatus 2000, as described in further detail hereinabove.

Then, the received 510 measured temperature value is sent 520 to a second computer (say a server computer), say by the temperature sender 220, as described in further detail hereinabove. The second computer is in communication with the device, with the computer coupled to the device, or with the computer in communication with the device, as described in further detail hereinabove.

The second computer receives the sent 520 measured temperature value and generates corrective data (say data defining a function) based on the measured temperature value and on data previously gathered on the second computer, as described in further detail hereinabove. Then, the second computer sends the corrective data to the device or computer that the sent 520 measured temperature value originates from.

Then, the corrective data generated by the second computer and sent from the second computer is received 530, say by the corrective data receiver 230 that may be implemented on the device, on the computer in communication with the device, or on the computer coupled to the device, as described in further detail hereinabove.

In a first example, the received 530 corrective data defines a function to be applied on the result of the measurement, for correcting the result, say by replacing the result with a corrected value, with a range of corrected values, with a value closest to the result but within that range, etc., as described in further detail hereinabove.

In a second example, the measured temperature value of the body part is sent 520 to the second computer together with a result of the measurement of the fluid sample, as described in further detail hereinabove.

In the second example, the corrective data includes the corrected result itself, say a corrected value to replace the result with, a range of values to replace the result with, a range of values to be used for replacing the result by choosing a value closest to the result but within the range, etc., as described in further detail hereinabove.

Finally, a measurement of content of the fluid sample by the device may be corrected 540 using the received 530 corrective data, say by the measurement corrector 240, as described in further detail hereinabove.

Optionally, the method further includes a step of measuring the value of the temperature of the body part of the subject, say by the temperature measurer and using the temperature meter (say a thermometer installed on the device used to take the sample or on a device used therewith), as described in further detail hereinabove.

In one example, the temperature meter is installed on the device used to take the fluid sample, and is adapted for measuring the temperature of the body part while the device is being used to take the fluid sample from the body part, as described in further detail hereinabove.

Optionally, the method further includes a step of taking the fluid sample (during, immediately before, or immediately after measuring the body part's temperature value), say by the sample taker, as described in further detail hereinabove.

Optionally, the method further includes a step of measuring the fluid sample's content (say the concentration of a specific pathogen in the fluid sample, and hence in the subject's body fluid), say by the content measurer, as described in further detail hereinabove.

The content may be measured, for example, using DNA polymerization, using another chemical process, etc., as described in further detail hereinabove.

Optionally, the method further includes changing the temperature of the body part into a predetermined value prior to taking the fluid sample from the body part using the device, say by the temperature controller, as described in further detail hereinabove, and as illustrated, for example using FIG. 3. The temperature may be predefined by a user or programmer, as described in further detail hereinabove.

Optionally, in the second exemplary method, there is further captured an image of the body part (say the user's finger, upper arm part, etc.) prior to the taking of the fluid sample from that body part, say using the image capturer (say a camera installed on the device), as described in further detail hereinabove.

Optionally, the captured image is then received—say by the image receiver of apparatus 2000, and is analyzed—say by the image analyzer of apparatus 2000, as described in further detail hereinabove.

Optionally, based on the analyzed image, the user is guided in taking the fluid sample, say by the user guider of apparatus 2000. The user may be guided using messages presented on a small screen, using vocal instructions given to the user using a speaker, etc., as described in further detail hereinabove.

Optionally, in the first exemplary method, there is alternatively or additionally measured an electric property of the fluid sample (say a one indicative of pH of the sample) taken from the body part, an optical property of the taken fluid sample (say a one indicative of hemoglobin content of the sample), etc., as described in further detail hereinabove.

Figure 6:
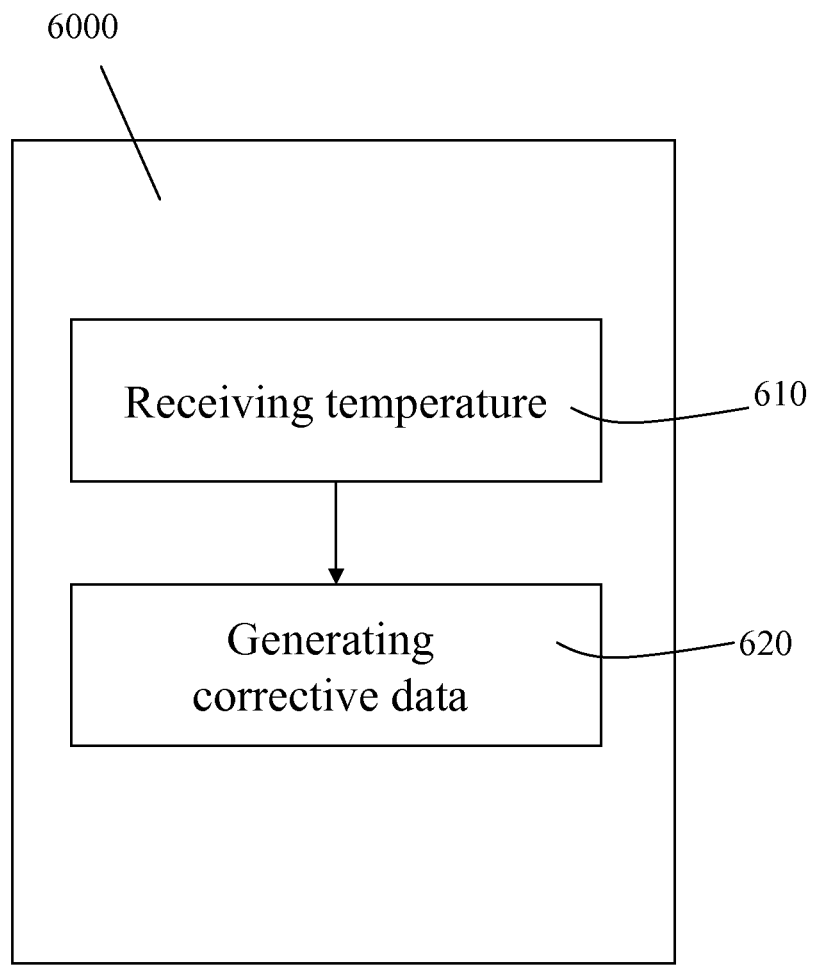
FIG. 6 is a simplified block diagram schematically illustrating a first non-transitory computer readable medium storing computer executable instructions for performing steps of measuring body fluid content, according to an exemplary embodiment of the present invention.

Reference is now made to FIG. 6, which is a simplified block diagram schematically illustrating a first non-transitory computer readable medium storing computer executable instructions for performing steps of measuring body fluid content, according to an exemplary embodiment of the present invention.

According to an exemplary embodiment of the present invention, there is provided a non-transitory computer readable medium 6000, such as a Micro SD (Secure Digital) Card, a CD-ROM, a USB-Memory, a Hard Disk Drive (HDD), a Solid State Drive (SSD), a computer's ROM chip, etc.

Optionally, the computer readable medium 6000 stores computer executable instructions, for performing steps of measuring body fluid content, say according to steps of the first exemplary method described in further detail hereinabove, and illustrated using FIG. 4.

The instructions may be executed on one or more computer processors.

The instructions may be executed for example, on a computer processor of device used to take fluid (say blood) samples from subjects (say persons, animals, etc.), say by the device of the sort described in further detail hereinbelow and illustrated using FIG. 3.

The instructions may also be executed implemented, for example, on a computer in communication with the device used to take the fluid samples, say on a server computer, as described in further detail hereinabove.

The computer executable instructions include a step of receiving 610 a measured value of a temperature of a body part of a subject. The temperature may be measured, for example, by the device used to take the fluid sample from the body part (say to take blood from a finger—i.e. from one of the narrow capillaries in the finger), by a device (say thermometer) used concurrently therewith when taking the sample, etc., as described in further detail hereinabove.

Optionally, with the measured value of the temperature of the subject's body part, there is further received 610 one or more additional parameters, say an ambient temperature value measured by the device when taking the sample, etc., and possibly, a measurement of a content of the fluid sample, to be corrected, as described in further detail hereinabove.

The computer executable instructions further include a step of generating 620 corrective data (say data defining a function having one or more parameters) based on the received 610 temperature value and on previously gathered data, as described in further detail hereinabove.

Optionally, the corrective data's generation 620 is further based on one or more additional parameters received 610 with the body part's measured temperature value, as described in further detail hereinabove.

The corrective data is usable for correcting a measurement of content of the fluid sample taken by the device, as described in further detail hereinabove.

Optionally, the computer executable instructions further include steps of taking the fluid sample, measuring the sample's content, correcting the measurement using the corrective data, other one or more of the first exemplary method's steps, or any combination thereof, as described in further detail hereinabove.

Figure 7:
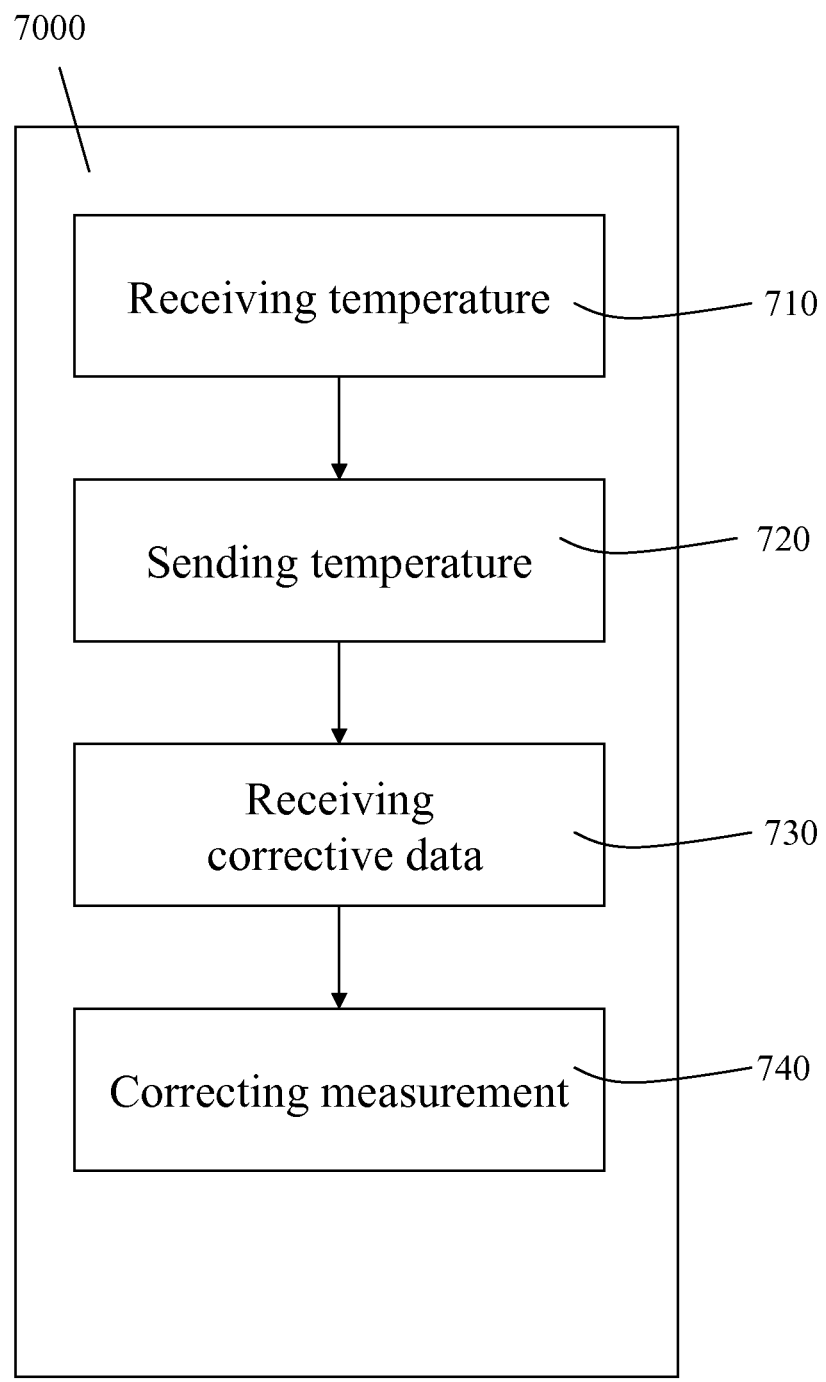
FIG. 7 is a simplified block diagram schematically illustrating a second non-transitory computer readable medium storing computer executable instructions for performing steps of measuring body fluid content, according to an exemplary embodiment of the present invention.

Reference is now made to FIG. 7, which is a simplified block diagram schematically illustrating a second non-transitory computer readable medium storing computer executable instructions for performing steps of measuring body fluid content, according to an exemplary embodiment of the present invention.

According to an exemplary embodiment of the present invention, there is provided a non-transitory computer readable medium 7000, such as a Micro SD (Secure Digital) Card, a CD-ROM, a USB-Memory, a Hard Disk Drive (HDD), a Solid State Drive (SSD), a computer's ROM chip, etc.

Optionally, the computer readable medium 7000 stores computer executable instructions, for performing steps of measuring body fluid content, say according to steps of the second exemplary method described in further detail hereinabove, and illustrated using FIG. 5.

Optionally, the method is implemented on a computer processor of device used to take fluid (say blood) samples from subjects (say persons, animals, etc.), say by the device of the sort described in further detail hereinabove and illustrated using FIG. 3.

Optionally, the method is implemented on a computer processor of a computer coupled to the device, of a computer that is in communication with the device over a short ranged connection (say over a local Area Network or Wi-Fi Connection), etc., as described in further detail hereinabove.

Optionally, the method is implemented on both the device and the computer coupled to the device or on both the device and the computer in communication with the device, say with some method steps implemented on the device and some method steps implemented on the computer, as described in further detail hereinabove.

The computer executable instructions include a step of receiving 710 a measured temperature value of a body part of a subject, say a temperature measured by the device used to take the fluid sample when taking the sample, as described in further detail hereinabove.

The computer executable instructions further include a steps of sending 720 the received 710 measured temperature value to a second computer (say a server computer). The second computer is in communication with the device, with the computer coupled to the device, or with the computer in communication with the device, as described in further detail hereinabove.

The second computer receives the sent 720 measured temperature value and generates corrective data (say data defining a function) based on the measured temperature value and data previously gathered on the second computer, as described in further detail hereinabove. Then, the second computer sends the corrective data to the device or computer that the measured temperature value originates from, as described in further detail hereinabove.

The computer executable instructions further include a step of receiving 730 the corrective data generated by the second computer and sent from the second computer, as described in further detail hereinabove.

In a first example, the received 730 corrective data defines a function to be applied on the result of the measurement, for correcting the result, say by replacing the result with a corrected value, with a range of corrected values, with a value closest to the result but still within that range, etc., as described in further detail hereinabove.

In a second example, the measured temperature value of the body part is sent 720 to the second computer together with a result of the measurement of the fluid sample, as described in further detail hereinabove.

In the second example, the corrective data includes the corrected result itself, say a corrected value to replace the result with, a range of values to replace the result with, a range of value to be used for replacing the result by choosing a value closest to the result but within the range, etc., as described in further detail hereinabove.

The computer executable instructions may further include a step of correcting 740 the measurement of content of the fluid sample using the received 730 corrective data, as described in further detail hereinabove.

Optionally, the computer executable instructions further include steps of measuring the value of the temperature of the body part of the subject, taking the sample (during, immediately before, or immediately after measuring the body part's temperature value), measuring the sample's content, etc., or any combination thereof, as described in further detail hereinabove and illustrated using FIG. 5.

It is expected that during the life of this patent many relevant devices and systems will be developed and the scope of the terms herein, particularly of the terms "Computer", "Computer Processor", "PCR", "DNA Polymerization", "Lab-on-a-Chip (LOC)", "Micro-Fluidic Chip", "Thermoelectric Cooler (TEC)", "Micro SD (Secure Digital) Card", "CD-ROM", "USB-Memory", "Hard Disk Drive (HDD)", "Solid State Drive (SSD)", "ROM Chip", "Wi-Fi", and "Internet", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

In addition, citation or identification of any reference in this application shall not be construed as an admission that such reference is available as prior art to the present invention.

What is claimed is:

1. A method of measuring body fluid content, the method comprising:
    by a device used for measuring body fluid sample content, guiding a user when taking a body fluid sample from a subject, based on an image of a body part;
    by the device, measuring content of the body fluid sample taken from the subject;
    by the device, measuring a value of a temperature of the subject using a temperature meter;
    by the device, generating corrective data based on the measured temperature value; and
    by the device, correcting a result of said measuring of the content of the body fluid sample taken from the subject, using the generated corrective data.

2. The method of claim 1, wherein said correcting comprises replacing the result of said measuring of the content with a range of values based on the corrective data.

3. The method of claim 1, wherein said correcting comprises changing the result of said measuring of the content only when the result is not within a range of values based on the corrective data.

4. The method of claim 1, wherein said generating of the corrective data is based on data received from a computer in communication with the device.

5. The method of claim 4, further comprising forwarding the measured value of the temperature of the subject to the computer that is in communication with the device, wherein the data received from the computer that is in communication with the device, is data generated on the computer that is in communication with the device, based on the measured temperature value.

6. The method of claim 1, wherein the corrective data is further based on previously gathered data, the previously gathered data comprising for each one of a plurality of previously taken test samples, a respective temperature value measured when taking the test sample and a respective content value measured using the test sample.

7. The method of claim 1, wherein the corrective data is further based on previously gathered data, the previously gathered data comprising for each one of a plurality of previously taken test samples, a respective temperature value measured when taking the test sample, a respective content value measured using the test sample, and a respective time indication.

8. The method of claim 1, wherein the corrective data is further based on previously gathered data, the previously gathered data comprising for each one of a plurality of previously taken test samples, a respective temperature value measured when taking the test sample, a respective content value measured using the test sample, and an at least one other parameter value.

9. The method of claim 1, further comprising taking the body fluid sample from the subject.

10. The method of claim 1, further comprising receiving biometric data taken from a body part of the subject.

11. The method of claim 10, wherein the body part is a finger of the subject, the method further comprising receiving fingerprint data taken from the body part of the subject.

12. The method of claim 1, further comprising generating disease progress data based on the measured content and on previously gathered data.

13. The method of claim 12, wherein said generating of the disease progress data is based on data received from a computer in communication with a device.

14. The method of claim 1, further comprising a preliminary step of changing the temperature of the subject into a predetermined value prior to taking the body fluid sample.

15. The method of claim 1, further comprising capturing the image of the body part.

16. The method of claim 1, further comprising analyzing an image of a finger of the subject, and guiding the user when taking the fluid sample from the finger, based on said analyzing.

17. The method of claim 1, further comprising analyzing an image of a finger of the subject, and advising a user to take the fluid sample from another finger, based on said analyzing.

18. A non-transitory computer readable medium storing computer executable instructions for performing steps of measuring body fluid content, the steps comprising:
    on a device used for measuring body fluid sample content, guiding a user when taking a body fluid sample from a subject, based on an image of a body part;
    on the device, measuring content of the body fluid sample taken from the subject;
    on the device, measuring a value of a temperature of the subject, using a temperature meter;
    on the device, generating corrective data based on the measured temperature value; and
    on the device, correcting a result of said measuring of the content of the body fluid sample taken from the subject, using the generated corrective data.

19. The method of claim 1, wherein the subject is the user.

20. An apparatus for measuring body fluid content, the apparatus comprising:
    a computer processor installed on a device used for measuring body fluid sample content;
    a user guider, implemented on the computer processor, configured to guide a user when taking a body fluid sample from a subject, based on an image of a body part;

a content measurer, implemented on the computer processor, configured to measure a content of the body fluid sample taken from the subject;

a temperature receiver, configured to measure a value of a temperature of the subject, using a temperature meter;

a corrective data receiver, configured to receive corrective data generated based on the measured temperature value; and a measurement corrector, configured to correct a result of said measuring of the content of the body fluid sample taken from the subject, using the received corrective data.

\* \* \* \* \*